(12) United States Patent
Chauhan et al.

(10) Patent No.: US 7,635,778 B2
(45) Date of Patent: Dec. 22, 2009

(54) COMPOSITION, METHOD OF AUTHENTICATING, METHODS OF MAKING AUTHENTICATABLE COMPOSITIONS, AUTHENTICATABLE ARTICLES MADE THERE FROM

(75) Inventors: Yogendrasinh Chauhan, Gujarat (IN); Mahesh Chaudhari, Maharashtra (IN); Adil Dhalla, Maharashtra (IN); Sriramakrishna Maruvada, Evansville, IN (US); Shantaram Naik, Karnataka (IN); Vandita Pai-Paranjape, Evansville, IN (US); Philippe Schottland, Evansville, IN (US); Ganapati Shankarling, Karnataka (IN); Kiran Puthamane, Maharashtra (IN); Meerakani Sait, Tamil Nadu (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 478 days.

(21) Appl. No.: 11/015,352

(22) Filed: Dec. 17, 2004

(65) Prior Publication Data
US 2006/0131761 A1    Jun. 22, 2006

(51) Int. Cl.
*C07D 311/30* (2006.01)
(52) U.S. Cl. .................. 549/403; 549/400
(58) Field of Classification Search ............ 549/402, 549/393, 400, 389, 403
See application file for complete search history.

(56) References Cited

U.S. PATENT DOCUMENTS

| 4,127,669 | A | 11/1978 | Connor et al. | |
|---|---|---|---|---|
| 6,099,930 | A | 8/2000 | Cyr et al. | 428/64.1 |
| 6,296,911 | B1 | 10/2001 | Guillen | 428/29 |
| 6,514,617 | B1 | 2/2003 | Hubbard et al. | 428/412 |
| 2002/0149003 | A1 | 10/2002 | Lucht et al. | 252/408.1 |

FOREIGN PATENT DOCUMENTS

| DE | 4106029 | 11/1991 |
|---|---|---|
| EP | 0238305 | 9/1987 |
| JP | 2003019867 | 1/2003 |
| WO | WO 98/27080 | * 6/1998 |
| WO | WO 00/14736 | 3/2000 |
| WO | 03080759 | 10/2003 |

OTHER PUBLICATIONS

Bennett et al., Bioorg. Med. Chem., 2004, 12, 2079-2098.*
Beutler et al., J. Med. Chem, 1998, 41, 2333-2338.*
Amic et al., J. Chem. Inf. Comput. Sci., 37, 581-586.*
Ahmad et al., Phytochemistry, 1995, 38(5), 1305-1307.*
Balboul et al., Phytochemistry, 1997, 46(6), 1045-1049.*
Meyer et al., J. Med. Chem, 1991, 34, 736-746.*
Nagarajan et al., Ionics, 2004, 10, 109-112.*
Martini et al., Mycol. Res., 1997, 101(8), 920-922.*
Looker et al., J. Org. Chem. 1962, 381-389.*
Hamado et al., Bull. Chem. Soc. Jpn., 1980, 53, 2630-2633.*
Wang et al., J. Mat. Sci., 1998, 33, 1753-1757.*
Fougerousse et al., J. Org. Chem., 2000, 65(2), 583-586.*
Brzozowski et al., J. Med. Chem., 2002, 45(2), 430-437.*
Shobana et al., Ind. J. Chem., Sect B, 1988, 27B(10), 965-966 (Abstract).*
Clark-Lewis et al., Aust. J. Chem., 1976, 29(1), 191-201 (Abstract).*
DE4106029 Publication Date Nov. 7, 1991 "Stable Moulding and Spinning Material" (Abstract Only).
JP2003019867A Publication Date Jan. 21, 2003 "Optical Recording Medium" (Machine Translation Only).
International Search Report for PCT/US2005/043736, Date of Mailing Apr. 20, 2007.
Satish C. Gupta et al.; Photoreorganisation of Some Bischromones; Tetrahedron 58 (2002) 3095-3100.
Satish C. Gupta et al.;Photolysis of Xylylbischromones Tetrahedron 59 (2003) 3609-3612.
A.D. Roshal et al., Spectral and Acid-Base Features of 3,7-Dihydroxy-2,8-Diphenyl-4H,6H-Pyrano[3,2-G]Chromene-4,6-Dione (Diflavonol)—A Potential Probe for Monitoring the Properties of Liquid Phases; J. Org. Chem. 2003, 68, 5860-5869.

\* cited by examiner

*Primary Examiner*—Janet L Andres
*Assistant Examiner*—David E Gallis

(57) ABSTRACT

A composition comprising compound of formula I, a process for preparing the composition comprising compound of formula I, methods of authentication for an article comprising compound of formula I or compound of formula II, authentication technology for polymer based articles comprising compound of formula I or formula II, methods of facilitating such authentication and method of making articles capable of authentication.

10 Claims, 5 Drawing Sheets

Compound of formula I                                   Compound of Formula II

Daylight

Ultraviolet light (365 nm)

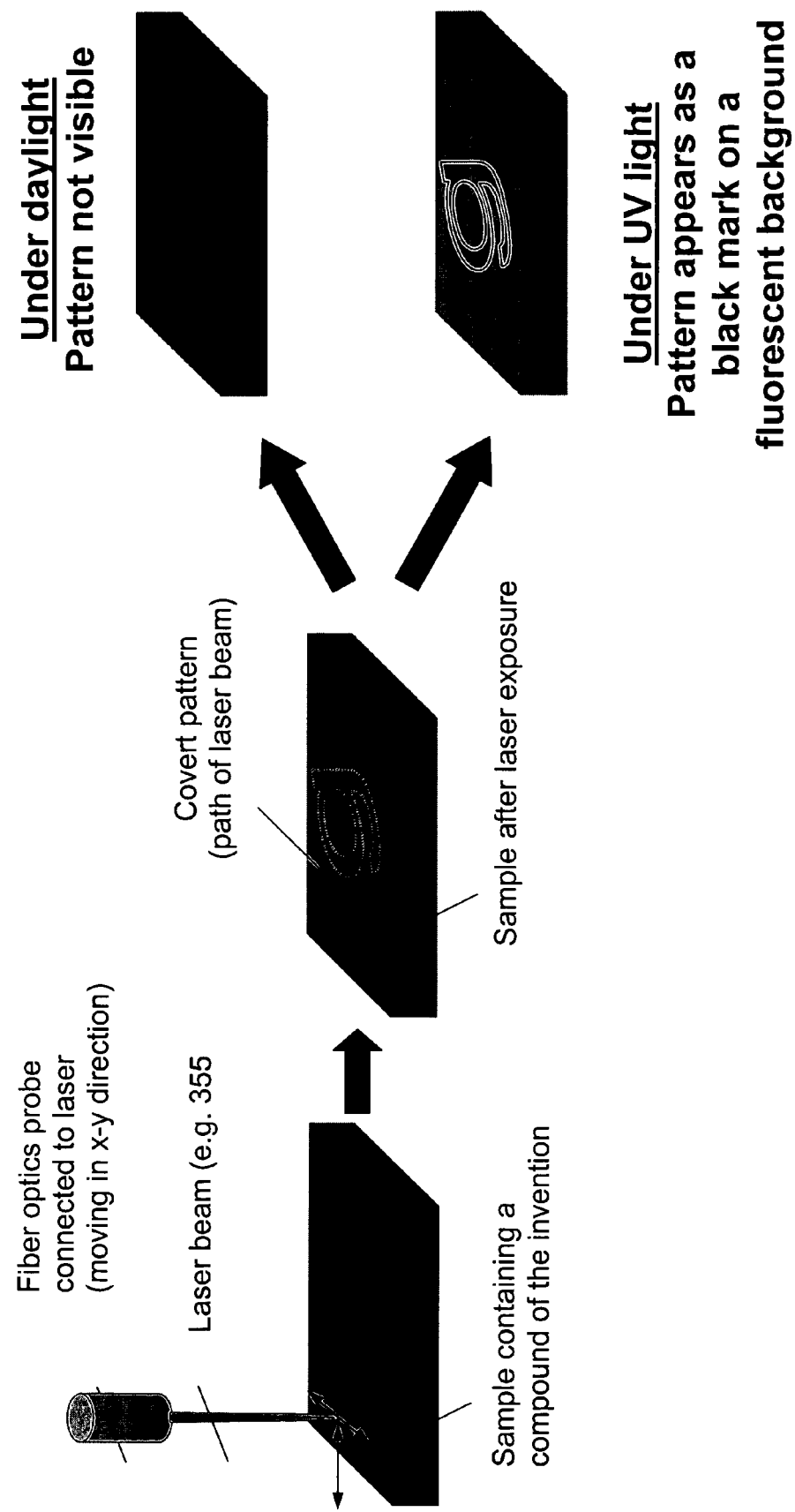

COMPOSITION, METHOD OF AUTHENTICATING, METHODS OF MAKING AUTHENTICATABLE COMPOSITIONS, AUTHENTICATABLE ARTICLES MADE THERE FROM

BACKGROUND OF INVENTION

The disclosure relates to a composition for authenticating an article and to authentication technology for polymer based articles. More particularly the disclosure relates to methods of authenticating polymer based articles, methods of facilitating such authentication, methods of making articles capable of authentication and processes for making the composition.

Data storage media or optical storage media traditionally contain information such as machine-readable code, audio, video, text, and/or graphics. Data storage media often include one or more substrates made of polymers such as polycarbonate.

A major problem confronting the various makers and users of data storage media is the unauthorized reproduction or copying of information by unauthorized manufacturers, sellers and/or users. Such unauthorized reproduction or duplication of data storage media is often referred to as piracy and can occur in a variety of ways, including consumer level piracy at the point of end use as well as whole sale duplication of data, substrate and anti-piracy information at the commercial level. Regardless of the manner, piracy of data storage media deprives legitimate software and entertainment content providers and original electronic equipment manufacturers significant revenue and profit.

Various attempts to stop piracy at the consumer level have included the placement of electronic anti-piracy signals on information carrying substrates along with the information sought to be protected. The machine readers and players of such data storage media are configured to require the identification of such anti-piracy signals prior to allowing access to the desired information. Theoretically, consumer level duplications are unable to reproduce these electronic anti-piracy signals on unauthorized copies and hence result in duplicates and copies that are unusable. However, numerous technologies to thwart such consumer level anti-piracy technologies have been and continue to be developed.

Makers and users of data storage media continue to seek new compositions and methods of tagging and authenticating data storage media substrates that are currently unknown and/or unavailable to unauthorized manufacturers, sellers, and/or users of data storage media. They are particularly interested in authentication markers or combinations of authentication markers for use in data storage media substrates that are difficult to obtain, reproduce, use, and/or find for the purposes of authenticating data storage media substrates and data storage media.

BRIEF SUMMARY

Disclosed herein is a composition comprising compounds of formula I:

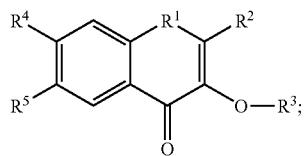

wherein $R^1$ is at least one of —O— or —NR$^6$—, wherein $R^6$ is a monovalent organic group;

$R^2$ is selected from the group consisting of an aromatic radical having 3 to 30 carbon atoms, and a cycloaliphatic radical having 3 to 12 carbon atoms;

$R^3$ is a labile moiety with the proviso that $R^3$ is not a group selected from the group consisting of —CH$_2$—(CH$_2$)$_n$—CH$_3$ and —CH$_2$—C$_6$H$_5$ wherein n has a value 0, 1 or 2; and $R^4$ and $R^5$ are either:

(i) independently at each occurrence selected from the group consisting of an aliphatic radical having 1 to 12 carbon atoms, an aromatic radical having 3 to 20 carbon atoms, a cycloaliphatic radical having 3 to 12 carbon atoms, a cyano group, a nitro group, a halo group, and a —OR$^9$ group, wherein $R^9$ is selected from the group consisting of hydrogen, an aliphatic radical having 1 to 12 carbon atoms, an aromatic radical having 3 to 20 carbon atoms, and a cycloaliphatic radical having 3 to 12 carbon atoms; or (ii) together represent an aromatic radical having 3 to 12 carbon atoms.

In one embodiment a process is provided for preparing a composition, wherein said process comprises a. reacting a compound of formula II;

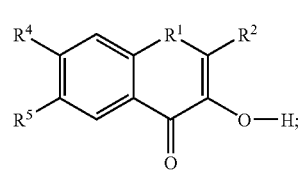

wherein $R^1$ is at least one of —O— or —NR$^6$—, wherein $R^6$ is a monovalent organic group;

$R^2$ is selected from the group consisting of an aromatic radical having 3 to 30 carbon atoms, and a cycloaliphatic radical having 3 to 12 carbon atoms;

$R^4$ and $R^5$ are either:

(i) independently at each occurrence selected from the group consisting of an aliphatic radical having 1 to 12 carbon atoms, an aromatic radical having 3 to 20 carbon atoms, a cycloaliphatic radical having 3 to 12 carbon atoms, a cyano group, a nitro group, a halo group, and a —OR$^9$ group, wherein $R^9$ is selected from the group consisting of hydrogen, an aliphatic radical having 1 to 12 carbon atoms, an aromatic radical having 3 to 20 carbon atoms, and a cycloaliphatic radical having 3 to 12 carbon atoms; or (ii) together represent an aromatic radical having 3 to 12 carbon atoms;

b. with a compound of formula III;

X—R$^3$           III wherein, $R^3$ is a labile moiety with the proviso that $R^3$ is not a group selected from the group consisting of —CH$_2$—(CH$_2$)$_n$—CH$_3$ and —CH$_2$—C$_6$H$_5$ wherein n has a value of 0, 1 or 2, and X is a leaving group.

c. in presence of a base and a solvent to form a compound of formula I,

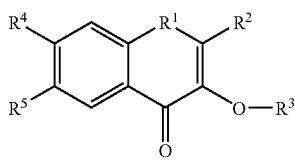

wherein $R^1$, $R^6$, $R^2$, $R^3$, $R^4$ and $R^5$ are as defined above.

In one other embodiment an authentication method comprises:
a. subjecting the article to a deblocking stimulus to obtain an at least partially deblocked authentication compound;
b. subjecting the article having the at least partially deblocked authentication compound to an excitation stimulus; and
c. measuring a response from the article.

In another aspect a method of making an authenticatable polymer comprises incorporating together a polymer and the above disclosed composition, wherein the above disclosed composition is incorporated in an amount of less than or equal to about 5 weight percent, based on the total weight of the authenticatable polymer.

In another aspect a method of authenticating that an article is an authenticatable article comprises subjecting an article comprising an authentication compound of formula II to an excitation stimulus; and measuring a response from the article with a detector.

In another aspect a method of making an authenticatable polymer comprises incorporating together a polymer and the above disclosed compound of formula II, wherein the above disclosed compound of formula II is incorporated in an amount of less than or equal to about 10 weight percent, based on the total weight of the authenticatable polymer.

Also disclosed is a method of making an article that comprises providing the disclosed authenticable polymer and forming an authenticable article from the authenticatable polymer.

BRIEF DESCRIPTION OF THE FIGURES

FIG. 5 indicates a method of generating a covert pattern in an article comprising the compound of formula I.

DETAILED DESCRIPTION

Figure 1:
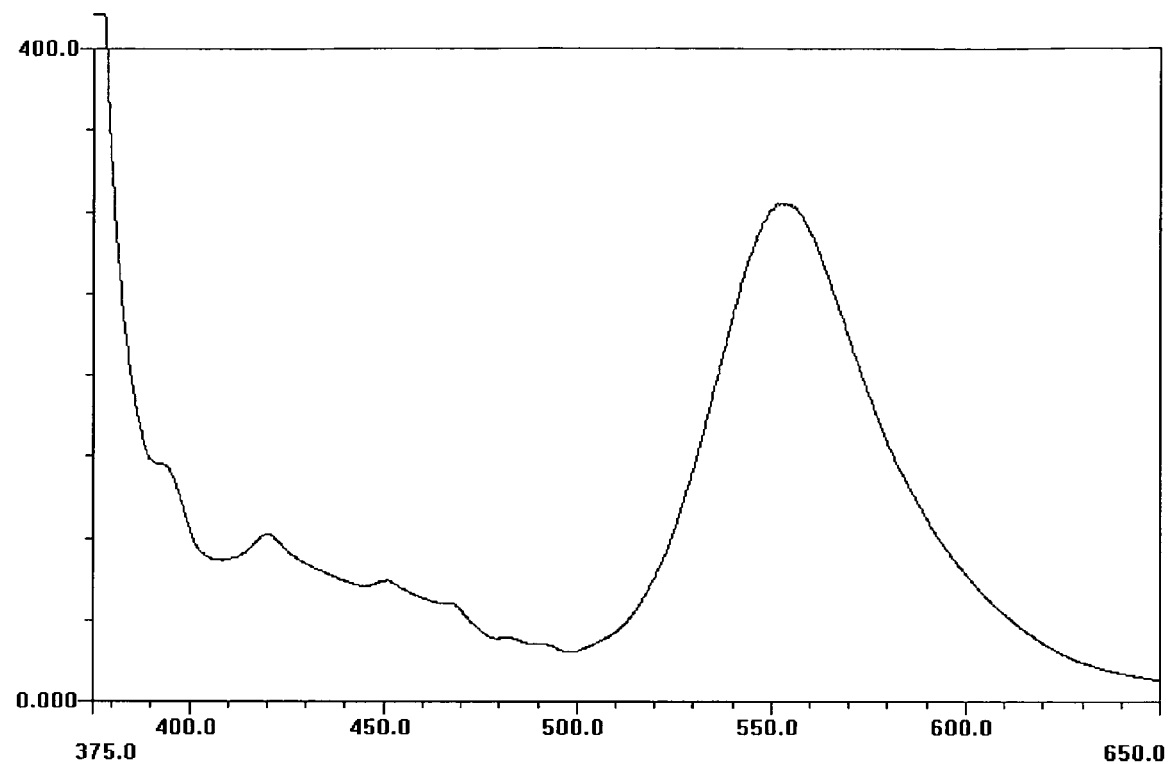
FIG. 1 represents the emission spectra for Bis-3HF. The fluorescence maximum is at a wavelength of about 553 nm nanometers (hereinafter at times referred to as nm) and the corresponding intensity of about 305.

The present disclosure may be understood more readily by reference to the following detailed description of preferred embodiments of the disclosure and the examples included therein. In the following specification and the claims which follow, reference will be made to a number of terms which shall be defined to have the following meanings:

The singular forms "a", "an" and "the" include plural references unless the context clearly dictates otherwise.

"Optional" or "optionally" means that the subsequently described event or circumstance may or may not occur, and that the description includes instances where the event occurs and instances where it does not.

The modifier "about" used in connection with a quantity is inclusive of the stated value and has the meaning dictated by the context (e.g., includes the degree of error associated with measurement of the particular quantity).

As used herein the term "aliphatic radical" refers to a radical having a valence of at least one comprising a linear or branched array of atoms, which is not cyclic. The array may include heteroatoms such as nitrogen, oxygen, sulfur, silicon, and phosphorous or may be composed exclusively of carbon and hydrogen. Examples of aliphatic radicals include methyl, methylene, ethyl, ethylene, hexyl, n-propyl, isopropyl, n-butyl, sec-butyl, tertiary-butyl, pentyl, neopentyl, hexyl, heptyl, octyl, nonyl, decyl, undecyl, dodecyl, hexamethylene, trifluoromethyl, trifluoroethyl, methoxy, ethyloxy, oxyethyleneoxy ($-O(CH_2)_2O-$), trimethylsilyl, mixtures thereof and the like. Aliphatic radicals may be substituted or unsubstituted and may comprise one or more substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, and the like.

As used herein the term "aromatic radical" refers to a radical having a valence of at least one comprising at least one aromatic group. Examples of aromatic radicals include phenyl, pyridyl, furanyl, thienyl, naphthyl, biphenyl, pyrrolyl, phenyl, hydroxy chromonyl phenyl, biphenylene and mixtures thereof. The term includes groups containing both aromatic and aliphatic and or cycloaliphatic components, for example a benzyl group or an indanyl group. Aromatic radicals may be substituted or unsubstituted and may comprise one or more heteroatoms including and/or substituents including amino groups, halogen atoms, cyano groups, nitro groups, hydroxyl groups, mercapto groups, $C_1$-$C_{10}$ alkyl groups, $C_1$-$C_{10}$ alkoxy groups, $C_1$-$C_{10}$ alkoxycarbonyl groups, $C_1$-$C_{10}$ alkylthio groups, $C_1$-$C_{10}$ alkylamino groups, mixtures thereof and the like.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical that comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. Cycloaliphatic radicals may be "substituted" or "unsubstituted". A substituted cycloaliphatic radical is defined as a cycloaliphatic radical that comprises at least one substituent. A substituted cycloaliphatic radical may comprise as many substituents as there are positions available on the cycloaliphatic radical for substitution. Substituents which may be present on a cycloaliphatic radical include but are not limited to halogen atoms such as fluorine, chlorine, bromine, and iodine. Substituted cycloaliphatic radicals include trifluoromethylcyclohexyl, hexafluoroisopropylidenebis(4-cyclohexyloxy) (i.e. —O $C_6H_{10}C(CF_3)_2C_6H_{10}O$—), chloromethylcyclohexyl; 3-trifluorovinyl-2-cyclopropyl; 3-trichloromethylcyclohexyl (i.e. 3-$CCl_3C_6H_{10}$—), bromopropylcyclohexyl (i.e. $BrCH_2CH_2CH_2$ $C_6H_{10}$—), and the like. For convenience, the term "unsubstituted cycloaliphatic radical" is defined herein to encompass a wide range of functional groups. Examples of suitable cycloaliphatic radicals include cyclobutyl, cyclopentyl, cyclohexyl, methylcyclohexyl, cycloheptyl, 4-allyloxycyclohexyl, aminocyclohexyl (i.e. $H_2NC_6H_{10}$—), aminocarbonylcyclopentyl (i.e. $NH_2COC_5H_8$—), 4-acetyloxycyclohexyl, dicyanoisopropylidenebis(4-cyclohexyloxy) (i.e. —O $C_6H_{10}C(CN)_2$ $C_6H_{10}O$—), 3-methylcyclohexyl, methylenebis(4-cyclohexyloxy) (i.e. —O $C_6H_{10}CH_2C_6H_{10}O$—), ethylcyclobutyl, cyclopropylethenyl, 3-formyl-2-terahydrofuranyl, 2-hexyl-5-tetrahydrofuranyl; hexamethylene-1,6-bis(4-cyclohexyloxy) (i.e. —O $C_6H_{10}(CH_2)_6C_6H_{10}O$—); 4-hydroxymethylcyclohexyl (i.e. 4-$HOCH_2C_6H_{10}$—), 4-mercaptomethylcyclohexyl (i.e. 4-$HSCH_2$ $C_6H_{10}$—), 4-methylthiocyclohexyl (i.e. 4-$CH_3SC_6H_{10}$—), 4-methoxycyclohexyl, 2-methoxycarbonylcyclohexyloxy (2-$CH_3OCOC_6H_{10}$—), nitromethylcyclohexyl (i.e. $NO_2CH_2C_6H_{10}$—), trimethylsilylcyclohexyl, t-butyldimethylsilylcyclopentyl, 4-trimethoxysilylethylcyclohexyl (e.g. $(CH_3O)_3SiCH_2CH_2C_6H_{10}$—), vinylcyclohexenyl, vinylidenebis(cyclohexyl), and the like. The term "a $C_3$-$C_{10}$ cycloaliphatic radical" includes substituted cycloaliphatic radicals and unsubstituted cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

Disclosed herein is a composition for authenticating an article. The disclosed composition may be referred to as an authenticating composition. Also disclosed is a process for making the composition. A method of authenticating an article comprising the composition is also disclosed. The disclosure also provides a polymer comprising the composition, an article made using the polymer and a method of making the article.

The use of the authenticatable polymers disclosed herein in various polymer based articles allows for one or more parties at any point along the manufacturing chain, distribution chain, point of sale or point of use of the article to confirm or identify the presence or absence of the disclosed composition in the authenticatable polymer or authenticatable article.

In one embodiment the composition comprises compounds of formula I:

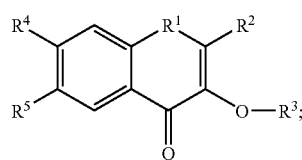

wherein $R^1$ is at least one of —O— or —$NR^6$—, wherein $R^6$ is a monovalent organic group $R^2$ is selected from the group consisting of an aromatic radical having 3 to 30 carbon atoms, and a cycloaliphatic radical having 3 to 12 carbon atoms;

$R^3$ is a labile with the proviso that $R^3$ is not a group selected from the group consisting of —$CH_2$—$(CH_2)_n$—$CH_3$ and —$CH_2$—$C_6H_5$ wherein n has a value 0, 1 or 2, and $R^4$ and $R^5$ are either:
(i) independently at each occurrence selected from the group consisting of an aliphatic radical having 1 to 12 carbon atoms, an aromatic radical having 3 to 20 carbon atoms, a cycloaliphatic radical having 3 to 12 carbon atoms, a cyano group, a nitro group, a halo group, and a —$OR^9$ group, wherein $R^9$ is selected from the group consisting of hydrogen, an aliphatic radical having 1 to 12 carbon atoms, an aromatic radical having 3 to 20 carbon atoms, and a cycloaliphatic radical having 3 to 12 carbon atoms; or
(ii) together represent an aromatic radical having 3 to 12 carbon atoms.

The monovalent organic radical $R^6$ is selected from the group consisting of hydrogen, an aliphatic radical having 1 to 12 carbon atoms, an aromatic radical having 3 to 20 carbon atoms, and a cycloaliphatic radical having 3 to 12 carbon atoms. In one embodiment $R^1$ in formula 1 may be —O—.

The labile moiety $R^3$ in the composition of formula I, may be defined as a moiety that disassociates itself from the parent compound, in this case, the compound of formula I, under the influence of one or more deblocking stimulus. Illustrative stimulus sufficient to cause the disassociation or deblocking of labile moiety $R^3$ from the compound of formula I include heat stimulus, photo stimulus, chemical stimulus, and mixtures of two or more of the foregoing deblocking stimuli.

The heat stimulus found suitable for disassociating a labile moiety $R^3$ typically comprises heating at least a portion of the authenticatable article comprising the composition defined above, to a temperature T1 sufficient to effect the disassociation or deblocking of the labile moiety $R^3$ from the compound of formula I. Illustrative temperatures T1 effective in achieving the dissociation of the labile moiety $R^3$ may range from about 70° C. to about 400° C. and may arise from direct or indirect sources of heat. In one embodiment the temperature T1 ranges from about 100° C. to about 400° C. In one exemplary embodiment the temperature T1 ranges from about 300° C. to about 400° C. Exemplary sources of direct heat include, but are not limited to thermal processes (such as heating the sample with a heat gun, heating bands, a hot plate, or an oven) where the sample is in direct contact with a heat flux, compounding, extrusion, and molding being processes that use high temperature that directly generate a heat flux as may be encountered in the process of manufacturing an article or an authenticating polymer. Indirect sources would generate heat inside the sample by transformation of another form of energy into heat. For instance, an energy beam (e.g. an infrared beam or a laser beam) would be absorbed by the sample and the energy absorbed would be dissipated into heat within the sample thus raising the temperature.

The photo stimulus found suitable for dissociating a labile moiety $R^3$ typically comprises exposing the authenticatable article to a photo source that emits a wavelength sufficient to dissociate the labile moiety $R^3$ from the composition. Illustrative examples of suitable wavelength include those from about 190 nm to 470 nm. In one embodiment, a suitable photo stimulus will have a wavelength of from about 250 nm to 470 nm. In another embodiment, a suitable photo stimulus will have a wavelength of from about 350 nm to about 450 nm. Alternatively, pressure lamps of wattage greater that 100 watts may be employed as the photo stimulus. In one embodiment a suitable pressure lamp will have a wattage greater than 120 watts. In another embodiment a suitable pressure lamp will have a wattage greater than 450 watts (W). Solid state lasers such as Nd:YAG lasers may be suitable for the deblocking (such laser could have wavelengths of 266 or 355 nm for instance). Diode lasers may be considered provided that their beam is absorbed by the sample (e.g. 532, 635, 650 or 780 nm) for instance when an additive is added with absorption properties at these wavelengths. High intensity discharge lamps (HID) may also be used. It should be noted that for all sources, the power and the time of exposure needs to be adapted to dissociate the labile moiety without significantly degrading the fluorophore formed (photobleaching). Optical filters may be used to block certain wavelengths to limit/prevent degradation.

Depending on the wavelength or wattage of the photo stimulus employed time taken for the dissociation of the labile moiety may vary. Typically the time taken is about 10 seconds to about 12 hours. In one embodiment the time taken varies from about 1 hour to 10 hours. In one particular embodiment the time taken varies from about 2 to 8 hours.

Illustrative examples of suitable photo stimulus include, but are not limited to, exposure to a ultraviolet-visible lamp having a wavelength greater than 320 nm at room temperature for a time period of 1 to 12 hours, a ultraviolet-near visible light emitting diode, a ultraviolet laser diode, a 450 W medium pressure lamp (Hanovia) with a pyrex filter sleeve under nitrogen atmosphere for 30-45 minutes and a 125 W high-pressure mercury lamp for 1-2 hours.

The chemical stimulus found suitable for dissociating a labile moiety $R^3$ typically comprises contacting the authenticatable article with an acid or a base depending on the type of labile moiety $R^3$ that needs to be dissociated.

In one embodiment for a labile moiety that dissociates in the presence of an acid, the dissociation occurs at a pH of 1 to 6, more specifically the pH is at 2 to 6. In one embodiment the pH is at 3 to 5. Illustrative acids that may be employed as the chemical stimulus include those selected from the group consisting of citric acid, phosphoric acid, hydrochloric acid, acetic acid and tetrafluoro acetic acid. In one embodiment the acid employed is phosphoric acid. In certain circumstances and for very specific applications e.g. in healthcare or for biosensor applications, the chemical stimulus could be an enzyme.

In one embodiment for a labile moiety that dissociated in the presence of a base, the dissociation occurs at a pH of 8 to 12; more specifically the pH is at 9 to 11. In one embodiment the pH is at 9-10. Illustrative bases that may be used as the chemical stimulus include those selected from the group consisting of sodium hydroxide, potassium hydroxide, piperidine in 20% dimethylformamide, piperazine, 1,8-diazabicyclo [5.4.0]undec-7-ene with 2% piperidine. In one embodiment the base employed is piperidine in 20% dimethylformamide.

The labile moiety $R^3$ that can effectively be dissociated from the compound of formula I may generally be any labile moiety that can be at least partially or totally disassociated or deblocked from the compound I as a result of exposure to the heat and/or photo and/or chemical stimulus discussed above. Illustrative examples of suitable labile moieties $R^3$ include those selected from the group consisting of —C(O)—O—$R^7$, —$CH_2$—$R^8$, —$SO_2$—$R^9$, —C(O)$R^{10}$, —C(S)—$R^{11}$, —C(O)—$NR^{12}R^{13}$ and —$SiR^{14}R^5R^{16}$; wherein $R^7$, $R^8$, $R^9$, $R^{10}$, $R^{11}$, $R^4$, $R^{15}$ and $R^{16}$ are independently selected from the group consisting of an aliphatic radical having 1 to 12 carbon atoms, a cycloaliphatic radical having 3 to 20 carbon atoms, and an aromatic radical having 3 to 20 carbon atoms and wherein $R^{12}$ and $R^{13}$ are independently at each occurrence selected from the group consisting of hydrogen, an aliphatic radical having 1 to 12 carbon atoms, a cycloaliphatic radical having 3 to 20 carbon atoms, and an aromatic radical having 3 to 20 carbon atoms, with the proviso that $R^3$ is not a group selected from the group consisting of —$CH_2$—$(CH_2)_n$—$CH_3$ and —$CH_2$—$C_6H_5$ wherein n has a value 0, 1 or 2. In one embodiment the labile moiety $R^3$, is selected from the group consisting of —C(O)—O—$R^7$, —$CH_2$—$R^8$, —$SO_2$—$R^9$ and —C(O)$R^{10}$, wherein $R^7$, $R^8$, $R^9$ and $R^{10}$ have the same meaning as defined above. In one exemplary embodiment, the labile moiety $R^3$ is selected from the group consisting of —C(O)—O—$R^7$ and —$CH_2$—$R^8$ wherein $R^7$ and $R^8$ are as defined above, with the proviso that $R^3$ is not a group selected from the group consisting of —$CH_2$—$(CH_2)_n$—$CH_3$ and —$CH_2$—$C_6H_5$ wherein n has a value of 0, 1 or 2.

Illustrative examples of the compound of formula I (hereinafter at times referred to as an authentication compound or the authentication compound of formula I) include, but are not limited to 3-ethylcarbonate-2-(4-(3-ethylcarbonate-4-oxo-4H-chromen-2-yl)phenyl)-4H-chromen-4-one, 3-phenylcarbonate-2-(4-(3-phenylcarbonate-4-oxo-4H-chromen-2-yl)phenyl)-4H-chromen-4-one, 3 tertbutylcarbonate-2-(4-(3-tertbutylcarbonate-4-oxo-4H-chromen-2-yl)phenyl)-4H-chromen-4-one, 3-butyloxycarbonyl-4H-1-benzopyran-4-one 3-tertbutylcarbonate-2-biphenyl-4H-chromen-4-one, terephthalic acid bis-(4-oxo-2-phenyl-4H-chromen-3-yl) ester, toluene-4-sulfonic acid-2-biphenyl-4-yl-4-oxo-4H-chromen-3-yl ester, and carbonic acid 2-biphenyl-4-yl-4-oxo-4H-chromen-3-yl ester 4-[1-(4-hydroxy-phenyl)-1-methyl-ethyl]-phenyl ester. In an exemplary embodiment the compound of formula I is 3ethylcarbonate-2-(4-(3-ethylcarbonate-4-oxo-4H-chromen-2-yl)phenyl)-4H-chromen-4-one.

In one embodiment a process for preparing the composition comprising a compound of formula I is provided. The process comprises reacting a compound of formula II;

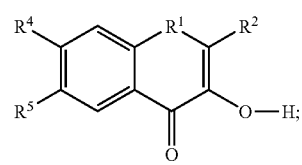

II with a compound of formula III;

 III wherein $R^1$, $R^2$, $R^3$, $R^4$ and, $R^5$ have the same meaning as defined above and X is a leaving group. Under the reaction conditions group X reacts with the hydrogen of group —OH in formula II thus facilitating the formation of compound of formula I. X includes any leaving group known in the prior art that can be associated with the labile moiety $R^3$. Illustrative examples of X include but are not limited to a halogen, an hydroxy group, a —$OR^{17}$ group or a —O—C(O)— linkage; wherein $R^{17}$ is an aliphatic radical. The above reaction is carried out in presence of a base and a solvent.

Illustrative examples of base employed in the reaction of compound of formula II with the compound of formula III includes, but are not limited, to triethylamine, pyridine, dimethylaminopyridine, lutidine (dimethylpyridine), piperidine and picoline. In one embodiment the base is selected form the group consisting of triethylamine and pyridine. In one exemplary embodiment the base is triethylamine.

Illustrative example of solvent employed in the reaction includes but are not limited to, dichloromethane, dichloroethane, monochlorobenzene, dichlorobenzene, tetrahydrofuran, dimethyl formamide and dimethyl acetamide. In one embodiment the solvent is selected from dichloromethane and dichloroethane. In one exemplary embodiment the solvent is dichloroethane. In one embodiment the compound of formula III, when used in excess, may function as the solvent.

The reaction parameters and reaction contents may vary based on the specific compound of formula I being prepared. The reaction temperature typically ranges from about −5° C. to about 100° C. The reaction temperature may vary dependant on the compound of formula II and compound of formula III being employed in the reaction.

Illustrative examples of the compound of formula II include but are not limited to 3-hydroxy-chromen-4-one, 3-hydroxy-1H-quinolin-4-one; 3-hydroxy-1-methyl-1H-quinolin-4-one; 3-hydroxy-2-phenyl-4H-chromen-4-one; 3-hydroxy-2-(4-(3-hydroxy-4-oxo-4H-chromen-2-yl)phenyl)-4H-chromen-4-one 3-hydroxy-2-(4'-(2-(3-phenoxycarbonyl chromonyl)))-phenyl-4H-1-benzopyran-4-one; 7-hydroxy-6-phenyl-1,5-dioxa-cyclopenta[b]naphthalene-8-one, 7-hydroxy-6-[4-(6-hydroxy-5-oxo-5H-furo[3,2-g]chromen-7-yl)-phenyl]-1,5-dioxacyclopenta[b]naphthalen-8-one (also known as 7-hydroxy-6-[4-(6-hydroxy-1-oxa-5-oxo-5H-furo[3,2-g]chromen-7-yl)-phenyl]-5-oxacyclopenta[b]naphthalen-8-one), 3,7-dihydroxy-2,8-diphenyl-pyrano[3,2-g]chromene-4,6-dione (also known as 3,7-dihydroxy-2,8-diphenyl-4H,6H-pyrano[3,2-g]chromene-4,6-dione), and 3-hydroxy-2-[4'-(3"-hydroxy-2"-thiophen-2yl-chromen-4"one)-phenyl]-2-chromen-4-one (also known as 3-hydroxy-2-(5-(3-hydroxy-4-oxo-4H-chromen-2yl)-thienyl)-4H-chromen-4-one). In one embodiment the compound of formula II is 3-hydroxy-chromen-4-one.

In one other embodiment the disclosure provides a method of authenticating that an article is an authenticatable article by identifying the presence of an authenticatable compound in the article. In one embodiment the authenticatable compound is a compound of formula I. In another embodiment the authenticatable compound is a compound of formula II. In one embodiment when the authenticating compound is a compound of formula I, the method of authenticating comprises subjecting the article to a deblocking stimulus, subsequently subjecting the article to an excitation stimulus and then measuring the response obtained using a detector. In one embodiment when the authenticating compound is a compound of formula II, the method of authenticating involves subjecting the article to an excitation stimulus and then measuring the response obtained using a detector.

In one embodiment an article comprising an authentication compound of formula I is subjected to a deblocking stimulus to obtain an article comprising an at least partially deblocked authentication compound. As referred to herein the term "deblocking stimulus" means, a stimulus strong enough to disassociate the labile moiety $R^3$ present in the compound of formula I, to provide its parent compound i.e. the corresponding compound of formula II. As described above the heat and/or photo and/or chemical stimulus function as the deblocking stimulus to provide an article comprising an at least partially deblocked authentication compound.

The resultant article comprising an at least partially deblocked authentication compound is subsequently subjected to an excitation stimulus. Subjecting the article to the excitation stimulus results in the emission of a signature signal from the at least partially deblocked authentication compound present in the article. In one embodiment, the excitation stimulus may be a photo stimulus having a wavelength less than or equal to the visible cut-off wavelength. As referred to herein the visible cut-off wavelength the highest wavelength above the absorption maximum for which the absorption intensity is equal to 5% of the maximum absorption intensity. This means that 95% of the absorption will be at or below cut-off wavelength.

In one embodiment the excitation stimulus has a wavelength ranging from about 250 nm to about 450 nm. In one other embodiment the excitation stimulus has a wavelength ranging from about 275 nm to about 440 nm. In a particular embodiment the excitation stimulus has a wavelength ranging from about 335 nm to about 435 nm. Illustrative examples of excitation stimulus are selected from the group consisting of a ultraviolet-visible lamp; a light emitting diode (hereinafter at times referred to as LED); a laser diode; a combination of at least two light emitting diodes and a combination of ultraviolet radiation source and a white light emitting diode and a combination of any of the foregoing. In one embodiment an ultraviolet-visible lamp at a wavelength of about 340 nanometers to about 390 nanometers is employed as the excitation stimulus. In one preferred embodiment, the excitation stimulus is a light emitting diode with a peak wavelength located between about 350 and about 435 nm. In one specific embodiment, the stimulus is a light emitting diode with a peak at about 380 nm. Several light sources (such as LEDs) can be used separately to generate an optical response. In one embodiment, a white LED and a UV LED is used instead of single source. In one other embodiment a white LED, a UV LED and a blue LED is used because it allows for an easier distinction between long Stokes shift fluorophores and counterfeits using regular fluorophores.

On being subjected to the excitation stimulus the authentication compound of formula I or formula II, contained in the article gives out a signal. 'Signal' as used herein refers to a response detectable by an analytical method such as vibrational spectroscopy, fluorescence spectroscopy, luminescence spectroscopy, electronic spectroscopy and the like and combinations thereof. In one exemplary embodiment, signal refers to a response detectable by an analytical method such as fluorescence spectroscopy, luminescence spectroscopy, and the like and combinations thereof. In another exemplary embodiment, signal refers to a response detectable by fluorescence spectroscopy. This signal is characteristic of the authentication compound of formula I in the at least partially deblocked or totally deblocked state and the authentication compound of formula II, and is hereinafter referred to as the signature signal.

The signal obtained from an article comprising authentication compound of formula II may be considered as the reference signal, since compound of formula II is the parent compound for the compound of formula I. The signature signal obtained from an article containing an authentication compound of formula I is determined by comparing with the reference signal obtained from an article containing the corresponding parent compound of formula II under comparable excitation conditions i.e. the response obtained from the authentication compound and the parent compound of formula II when both are subjected to an excitation stimulus of the same wavelength and same intensity and the resultant responses are compared.

The signature signal (hereinafter at times referred to as the response) from the at least partially deblocked compound, on being subjected to the excitation stimulus is measured with a detector. It is then determined if the response is comparable to the response obtained from a compound of formula II (which is the unblocked form of the at least partially deblocked corresponding compound of formula I). The authentication of the authenticatable article can be performed at least once which would result in the at least partially deblocked authentication compound. Since the authentication compound contained in the article may be selectively partially deblocked and only the deblocked region responds to the excitation stimulus the authentication compound contained in the article can be selectively subjected to multiple deblocking steps until the authentication compound contained in the article is totally deblocked.

The deblocking stimulus is generally sufficient to result in at least a partial deblocking. This provides an at least partially deblocked authentication compound. The authentication compound may be considered to be partially deblocked when the signature signal obtained at a comparative concentration and a comparative wavelength, has an emission intensity of less than or equal to 99%, of the emission intensity of the compound of formula II i.e. the parent unblocked compound. In one embodiment the partially deblocked authentication compound has an emission intensity of less than 95% of the emission intensity of the compound of formula II i.e. the parent unblocked compound. In another embodiment, the partially deblocked authentication compound has an emission intensity of less than 90% of the emission intensity of the compound of formula II i.e., the parent unblocked compound. In one embodiment, the partially deblocked authentication compound has an emission intensity of less than 80% of the emission intensity of the compound of formula II i.e., the parent unblocked compound. In another embodiment the authentication compound may be considered to be totally deblocked when the signature signal at a comparative concentration and a comparative wavelength has an emission intensity of greater than 95% of the emission intensity of the compound of formula II. In one other embodiment the authentication compound may be considered to be totally deblocked when the signature signal at a comparative concentration and a comparative wavelength has an emission intensity of greater than 99% of the emission intensity of the compound of formula II.

The advantage of having a partially deblocked or a fully deblocked authentication compound may help to exercise a control on the signature signal, thus rendering counterfeiting more difficult. In addition a contrast may be achieved in the same article between the partially or fully deblocked regions and the unblocked region, i.e. the region where the compound of formula I has not been subjected to a deblocking stimulus. This would be advantageous in authenticating the article using symbols, emblems, markings and the like to create a covert pattern that would be revealed under an excitation stimulus.

The signature signal emitted from the stimulated portion of the authenticated article is measured with a detector. The signature signal is characteristic of the authenticated compound present in the authenticated article. The intensity of the signature signal varies depending on the degree of deblocking of the authentication compound of formula I, when the article containing the compound is subjected to a deblocking stimulus. The intensities vary as described above and are gauged based on the emission intensity of the article comprising the corresponding compound of formula II.

The signature signal is detected or evaluated using a detector. Typically the detector employed comprises a photodetector that can detect the change in wavelength and intensity of the signature signal as compared to the excitation stimulus. Typically the detector employed is capable of detecting the signature signal having a peak wavelength of greater that about 470 nm. In one embodiment the detector is capable of detecting the signature having a peak wavelength of greater than about 450 to about 650 nm. In a preferred embodiment the detector is capable of detecting the signature signal having a wavelength of greater than about 470 to about 600 nm.

In one embodiment the photodetector is the most easily available detector i.e. the photo response detected by an unaided human eye.

In one other embodiment the photodetector is a photodiode. In one other embodiment an array of photodiodes may be used, which array is capable of capturing a plurality of wavelengths to better identify the emission. In one embodiment the detector comprises a photodetector comprising a combination of photodiodes capable of measuring color typically when the excitation stimulus comprises a combination of at least two light emitting diodes or a combination of ultraviolet radiation source and a white light emitting diode. In one embodiment, the photodiode array capable of measuring color includes a red, green blue and a clear filtered photodiode.

In one other embodiment the detector comprises a photodetector that measures the signature signal generated due to each of the excitation stimulus.

In one embodiment the step of measuring the response of the article with a photodetector comprises measuring the resultant fluorescence. The fluorescence may be measured in the transmission mode, reflectance mode or in the emission mode. In one embodiment the fluorescence is measured in the reflectance mode. The response of the article may be measured using an analytical technique that is selected from the group consisting of fluorescence spectroscopy, luminescence spectroscopy, vibrational spectroscopy and electronic spectroscopy. In one embodiment the step of measuring the response of the article comprises performing fluorescence spectroscopy or luminescence spectroscopy.

The signature signal elicited form the authentication compound when the article containing the authentication compound is subjected to an excitation stimulus is a result of the long Stoke's shift that the excitation stimulus undergoes when contacted with the authentication compound. Fluorescent molecules absorb light at one wavelength and emit light at another, longer wavelength. When fluorescent molecules absorb a photon of a molecule specific wavelength an electron in a given orbital rises to a higher energy level (the excited) state. Electrons in this state are unstable and will return to the ground state, releasing energy in the form of light and heat. This emission of energy in the form of light is fluorescence. Because some energy is lost as heat, the emitted light contains less energy and therefore has a longer wavelength than the absorbed (or excitation) light. The notable shift between excitation stimulus and emitted light is called Stokes shift. Typically the signature signal obtained from the article has a peak wavelength of greater than or equal to 470 nanometers and less than or equal to 650 nanometers. In one embodiment the signature signal has wavelength of greater than or equal to 500 nm and less than or equal 620 nm. In one particular embodiment the wavelength is greater that or equal to 520 nm and less than or equal to 600 nm. The absorption is at about 250 nm to 450 nm and the emission is greater than or equal to 470 nm, which indicates a long stokes shift. The Stokes shift is typically considered as long when it exceeds 50 nm. The chromones typically have shifts >100 nm which are very long.

The signature signal of the stimulated portion of the article containing the at least partially deblocked compound of formula I to be authenticated is compared with a reference signal corresponding to an article containing the corresponding parent compound of formula II i.e. the reference compound. This comparison comprises comparing the intensity of fluorescence, the shape of the fluorescence peaks, the location of the fluorescence peaks, the duration or decay of fluorescence over time or after removal of heat source, the ratio of fluorescence intensity at two different wavelengths or combinations of the above.

Typically the difference in the fluorescence intensity of the photo detectable signature signal and the reference signal, when similar excitation stimulus is employed, are compared. For example both the article and the reference article are subjected to ultraviolet-visible radiation at a wavelength of 365 nanometers and the location and intensities of the resultant signature signal and reference signal are compared. As described above the authentication compound may be considered to be partially deblocked when the signature signal obtained at a comparative concentration and a comparative wavelength, has an emission intensity of less than or equal to 99%, of the emission intensity of the reference compound i.e. the parent unblocked compound. In one embodiment emission intensity of less than 95% of the emission intensity of the reference compound. In another embodiment the emission intensity of less than 90% of the reference compound. In another embodiment the authentication compound may be considered to be totally deblocked when the signature signal at a comparative concentration and a comparative wavelength has an emission intensity of greater than 99% of the emission intensity of the reference compound.

In one embodiment the authenticatable article may be marked with a covert pattern as illustrated in FIG. 5. As used herein the covert pattern is a marking that is not visible when exposed to daylight but is easily discernable when placed under ultraviolet radiation. The covert pattern may be produced by using a laser source, for example a laser diode at a wavelength of about 350 nm to about 405 nm.

In one embodiment the authenticable composition may further comprise a polymer. Suitable polymers are selected form the group consisting of but not limited to amorphous, crystalline and semi-crystalline thermoplastic materials: polyvinyl chloride, polyolefins (including, but not limited to, linear and cyclic polyolefins and including polyethylene, chlorinated polyethylene, polypropylene, and the like), polyesters (including, but not limited to, polyethylene terephthalate, polybutylene terephthalate, polycyclohexylmethylene terephthalate, and the like), polyamides, polysulfones (including, but not limited to, hydrogenated polysulfones, and the like), polyimides, polyether imides, polyether sulfones, polyphenylene sulfides, polyether ketones, polyether ether ketones, ABS resins, polystyrenes (including, but not limited to, hydrogenated polystyrenes, syndiotactic and atactic polystyrenes, polycyclohexyl ethylene, styrene-co-acrylonitrile, styrene-co-maleic anhydride, and the like), polybutadiene, polyacrylates (including, but not limited to, polymethylmethacrylate, methyl methacrylate-polyimide copolymers, and the like), polyacrylonitrile, polyacetals, polycarbonates, polyphenylene ethers (including, but not limited to, those derived from 2,6-dimethylphenol and copolymers with 2,3, 6-trimethylphenol, and the like), ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, as well as thermosetting resins such as epoxy, phenolic, alkyds, polyester, polyimide, polyurethane, mineral filled silicone, bis-maleimides, cyanate esters, vinyl, and benzocyclobutene resins, in addition to blends, copolymers, mixtures, reaction products and composites comprising a of the foregoing plastics. In an exemplary embodiment the polymer is a polycarbonate.

As used herein, the terms "polycarbonate", "polycarbonate composition", and "composition comprising aromatic carbonate chain units" includes compositions having structural units of the formula IV:

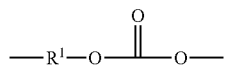

IV in which at least about 60 percent of the total number of R1 groups are aromatic radicals and the balance thereof are aliphatic, cycloaliphatic, or aromatic radicals. Preferably, R1 is an aromatic radical and, more preferably, a radical of the formula V:

V wherein $A^1$ and $A^2$ are independently at each occurrence a monocyclic divalent aromatic radical and $Y^1$ is a bridging radical having one or two atoms which separate $A^1$ from $A^2$. In an exemplary embodiment, one atom separates $A^1$ from $A^2$. Illustrative, non-limiting examples of radicals of this type are —O—, —S—, —S(O)—, —S(O2)—, —C(O)—, methylene, cyclohexyl-methylene, 2-[2,2,1]-bicycloheptylidene, ethylidene, isopropylidene, neopentylidene, cyclohexylidene, cyclopentadecylidene, cyclododecylidene, and adamantylidene. The bridging radical $Y^1$ can be a hydrocarbon group or a saturated hydrocarbon group such as methylene, cyclohexylidene or isopropylidene.

Polycarbonates can be produced by the interfacial reaction of dihydroxy compounds in which only one atom separates $A^1$ and $A^2$. As used herein, the term "dihydroxy compound" includes, for example, bisphenol compounds having general formula VI as follows:

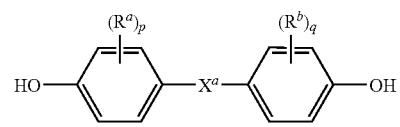

VI wherein $R^a$ and $R^b$ each represent a halogen atom or a monovalent hydrocarbon group and may be the same or different; and $X^a$ represents one of the groups of formula VII:

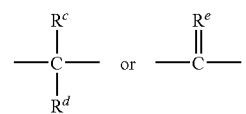

VII wherein $R^c$ and $R^d$ each independently represent a hydrogen atom or a monovalent linear or cyclic hydrocarbon group, $R^e$ is a divalent hydrocarbon group and a, b, c, d, e, p and q are each independently integers from 0 to 4.

Some illustrative, non-limiting examples of suitable dihydroxy compounds include dihydric phenols and the dihydroxy-substituted aromatic hydrocarbons disclosed by name or formula (generic or specific) in U.S. Pat. No. 4,217,438. A nonexclusive list of specific examples of the types of bisphenol compounds that may be represented by formula VI include the following: 1,1-bis(4-hydroxyphenyl)methane; 1,1-bis(4-hydroxyphenyl)ethane; 2,2-bis(4-hydroxyphenyl) propane (hereinafter "bisphenol A" or "BPA"); 2,2-bis(4-hydroxyphenyl)butane; 2,2-bis(4-hydroxyphenyl)octane; 1,1-bis(4-hydroxyphenyl)propane; 1,1-bis(4-hydroxyphenyl)n-butane; bis(4-hydroxyphenyl)phenylmethane; 2,2-bis (4-hydroxy-1-methylphenyl)propane; 1,1-bis(4-hydroxy-t-butylphenyl)propane; bis(hydroxyaryl)alkanes such as 2,2-bis(4-hydroxy-3-bromophenyl)propane; 1,1-bis(4-hydroxyphenyl)cyclopentane; and bis(hydroxyaryl) cycloalkanes such as 1,1-bis(4-hydroxyphenyl)cyclohexane; and the like as well as combinations comprising the foregoing.

It is also possible to employ two or more different dihydric phenols or a copolymer of a dihydric phenol with a glycol or with a hydroxy or acid-terminated polyester or with a dibasic acid or with a hydroxy acid in the event a carbonate copolymer rather than a homopolymer is desired for use. Polyarylates and polyester-carbonate resins or their blends can also be employed. Branched polycarbonates are also useful, as well as blends of linear polycarbonate and a branched polycarbonate. The branched polycarbonates may be prepared by adding a branching agent during polymerization.

These branching agents are well known and may comprise polyfunctional organic compounds containing at least three functional groups which may be hydroxyl, carboxyl, carboxylic anhydride, haloformyl and mixtures comprising a of the foregoing. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha,alpha-dimethyl benzyl) phenol), 4-chloroformyl phthalic anhydride, trimesic acid and benzophenone tetracarboxylic acid, and the like. The branching agents may be added at a level of about 0.05 to about 2.0 weight percent. Branching agents and procedures for making branched polycarbonates are described in U.S. Pat. Nos. 3,635,895 and 4,001,184. All types of polycarbonate end groups are herein contemplated.

In one embodiment, the polymer is a polycarbonate based on bisphenol A, in which each of $A^1$ and $A^2$ is p-phenylene and $Y^1$ is isopropylidene. In one embodiment, the average molecular weight of the polycarbonate is about 5,000 to about 100,000. In another exemplary embodiment, the average molecular weight of a polycarbonate used as the polymer may be about 10,000 to about 65,000, while in another exemplary embodiment, a polycarbonate used as the polymer may have an average molecular weight of about 15,000 to about 35,000.

In monitoring and evaluating polycarbonate synthesis, it is of particular interest to determine the concentration of Fries product present in the polycarbonate. Polycarbonates produced by a melt process or activated carbonate melt process such of those listed in U.S. Pat. Nos. 5,151,491 and 5,142,018 typically contain a significantly higher concentration of Fries product. As noted, the generation of significant Fries product can lead to polymer branching, resulting in uncontrollable melt behavior. As used herein, the terms "Fries" and "Fries product" denote a repeating unit in polycarbonate having the formula VIII:

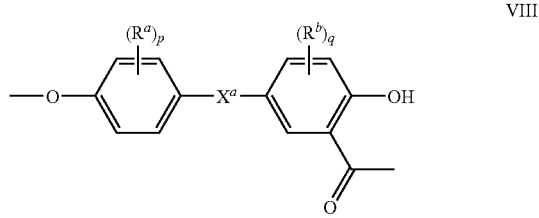

VIII wherein $X^a$ is a bivalent radical as described in connection with Formula VI described above.

Polycarbonate compositions suitable for use as the substrate polymer may also include various additives ordinarily incorporated in resin compositions of this type. Such additives are, for example, fillers or reinforcing agents; heat stabilizers; antioxidants; light stabilizers; plasticizers; antistatic agents; mold releasing agents; additional resins; blowing agents; and the like, as well as combinations comprising of the foregoing additives. Examples of fillers or reinforcing agents include glass fibers, asbestos, carbon fibers, silica, talc and calcium carbonate. Examples of heat stabilizers include triphenyl phosphite, tris-(2,6-dimethylphenyl)phosphite, tris-(mixed mono- and di-nonylphenyl)phosphite, dimethylbenene phosphonate and trimethyl phosphate. Examples of antioxidants include octadecyl-3-(3,5-di-tertiary-butyl-4-hydroxyphenyl)propionate, and pentaerythrityl-tetrakis[3-(3,5-di-tertiary-butyl-4-hydroxyphenyl)propionate]. Examples of light stabilizers include 2-(2-hydroxy-5-methylphenyl)benzotriazole, 2-(2-hydroxy-5-tertiary-octylphenyl)-benzotriazole and 2-hydroxy-4-n-octoxy benzophenone. Examples of plasticizers include dioctyl-4,5-epoxy-hexahydrophthalate, tris-(octoxycarbonylethyl)isocyanurate, tristearin and epoxidized soybean oil. Examples of the antistatic agent include glycerol monostearate, sodium stearyl sulfonate, and sodium dodecylbenzenesulfonate. Examples of mold releasing agents include stearyl stearate, beeswax, montan wax and paraffin wax. Examples of other resins include but are not limited to polypropylene, polystyrene, polymethyl methacrylate, and polyphenylene oxide. Combinations of any of the foregoing additives may be used. Such additives may be mixed at a suitable time during the mixing of the components for forming the composition.

The authenticatable compound of formula I is added to the polymer in an amount sufficient to be detected by an analytical method as discussed above. In one embodiment, the authenticatable compound of formula I may be present in the authenticatable polymer in an amount of no more than or equal to about 10.0% by weight, based on the weight of the authenticatable polymer. In another embodiment, the authenticatable compound of formula I may be present in the authenticatable polymer in an amount of less than or equal to about 5.0% by weight, based on the weight of the authenticatable polymer. In one embodiment, the authenticatable compound of formula I may be present in the authenticatable polymer in an amount of about 0.005% by weight, based on the weight of the authenticatable polymer. In one embodiment, the authenticatable compound of formula I may be present in the authenticatable polymer in an amount equal to about 1 part per billion (ppb). In an exemplary embodiment the amount is about 1 parts per million (ppm) to about 0.2 wt %. Effectively the concentration of the authenticatable compound should be sufficient to allow the detection of the signal over the noise of the background. If the detector is the human eye, this means that the emission is sufficient to be visually detectable. When a detector other than the human eye is used, it is preferred to have a signal to noise ratio greater than about 5, more specifically greater than about 20 and even more specifically greater than about 50. That is, the amount of the authentitcatable compound of formula I in the authenticatable polymer does not result in a color change apparent to the unaided human eye when the authenticatable polymer is exposed to an excitation stimulus under the conditions of an excitation stimulus.

In one exemplary embodiment a method is provided for making an authenticatable polymer. The method comprises incorporating together a polymer and a composition comprising an authenticable compound of formula 1, to provide an authenticable polymer. The amount of compound 1 employed is in an amount of about 1 parts per million (ppm) to about 0.2 wt %.

In addition to the polymer and the authenticatable compound of formula I, the authenticatable polymers disclosed herein may optionally include various additives ordinarily incorporated in resin compositions of this type. Such additives may include antioxidants, heat stabilizers, flame retardants, UV stabilizers, anti-static agents (tetra alkylammonium benzene sulfonate salts, tetra alkylphosphonium benzene sulfonate salts, and the like), mold releasing agents (pentaerythritol tetrastearate; glycerol monostearate, and the like), and the like, and combinations comprising the foregoing. For example, the authenticatable polymer composition can comprise heat stabilizer from about 0.01 weight percent to about 0.1 weight percent; an antistatic agent from about 0.01 weight percent to about 1 weight percent; and a mold releasing agent from about 0.1 weight percent to about 1 weight percent of a mold releasing agent; based upon the total weight of the authenticatable polymer.

Some possible antioxidants include, for example, organophosphites, e.g., tris(nonyl-phenyl)phosphite, tris(2,4-di-t-butylphenyl)phosphite, bis(2,4-di-t-butylphenyl)pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tertiary-butyl-4-hydroxyhydrocinnamate)]methane, 3,5-di-tertiary-butyl-4-hydroxyhydrocinnamate octadecyl, 2,4-di-tertiary-butylphenyl phosphite, and the like; butylated reaction products of para-cresol and dicyclopentadiene; alkylated hydroquinones; hydroxylated thiodiphenyl ethers; alkylidene-bisphenols; benzyl compounds; esters of beta-(3,5-di-tertiary-butyl-4-hydroxyphenyl)-propionic acid with monohydric or polyhydric alcohols; esters of beta-(5-tertiary-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tertiary-butyl-4-hydroxyphenyl)-propionic acid; and the like, as well as combinations comprising a of the foregoing.

Other potential additives which may be employed comprise: stabilizers such as light and thermal stabilizers (e.g., acidic phosphorous-based compounds); hindered phenols; zinc oxide, zinc sulfide particles, or combination thereof; lubricants (mineral oil, and the like), plasticizers; among others, as well as combinations comprising a of the foregoing additives. As known in the art, colorants (dyes and pigments) may be used to achieve a specific appearance under daylight. Selection of the colorants depends on the polymer matrix, the application requirements. Colorants are preferably selected in order to minimize the interactions with the stimulus and emission wavelengths.

In order to aid in the processing of the authenticatable polymer, particularly when the polymer is polycarbonate, catalyst(s) may also be employed, namely in the extruder or other mixing device. The catalyst typically assists in controlling the viscosity of the resulting material. Possible catalysts include hydroxides, such as tetraalkylammonium hydroxide, tetraalkylphosphonium hydroxide, and the like, with diethyldimethylammonium hydroxide and tetrabutylphosphonium hydroxide preferred. The catalyst(s) can be employed alone or in combination with quenchers such as acids, such as phosphoric acid, and the like. Additionally, water may be injected into the polymer melt during compounding and removed as water vapor through a vent to remove residual volatile compounds.

The authenticatable polymers disclosed herein are produced by using a reaction vessel capable of adequately mixing various precursors, such as a single or twin screw extruder, kneader, blender, or the like.

Methods for incorporating the authenticable compound of formula 1 into the polymer include, for example, coating, admixing, blending, or copolymerisation. The authenticable compound of formula 1 can be incorporated into the polymer such that they are uniformly dispersed throughout the authenticatable polymer or such that they are dispersed on a portion of the authenticatable polymer. In one exemplary embodiment, the authenticable compound of formula 1 will be incorporated into the polymer such that they are uniformly dispersed throughout the authenticatable polymer. The authenticable compound of formula 1 can be incorporated into the polymer in the polymer manufacturing stage, during the polymer compounding step, during polymer processing into articles, or combinations thereof. In one embodiment, the authenticable compound of formula 1 may be introduced using a concentrate (i.e., master-batch) either during the polymer compounding stage or during the article forming.

For example, the polymer precursors for the polymer can be premixed with the authenticable compound of formula 1 (e.g., in a pellet, powder, and/or liquid form) and simultaneously fed through a hopper into the extruder, or authenticable compound of formula 1 can be optionally added in the feed throat or through an alternate injection port of the injection molding machine or other molding. Optionally, in one embodiment, a polymer can be produced and the authenticable compound of formula 1 may be dispersed on a portion of the polymer by coating, molding, or welding on a portion of an authenticatable polymer there to. In one exemplary embodiment, authenticable compound of formula 1 may be homogenously distributed unless it is placed in a carrier that is not miscible with the polymer.

In one embodiment, the authenticable compound of formula 1 is incorporated into the polymer by admixing, blending, compounding or copolymerisation. In one exemplary embodiment, the authenticable compound of formula 1 will be incorporated into the polymer by forming a dry blend of the authenticable compound of formula 1 with the polymer and compounding the resultant mixture In another embodiment, the authenticable compound of formula 1 may be incorporated into the substrate polymer by adding the authenticable compound of formula 1 in the melt during the compounding. In one embodiment, such additions may be done via a side feeder. In another exemplary embodiment, the authenticable compound of formula 1 may be incorporated by compounding using a twin-screw extruder and adding the authenticable compound of formula 1 to the melt via a side feeder.

When the polymer precursors are employed, the extruder should be maintained at a sufficiently high temperature to melt the polymer precursors without causing decomposition thereof. For polycarbonate, for example, temperatures of about 220° C. to about 360° C. may be used in one embodiment. In another embodiment temperatures of about 260° C. to about 320° C. may be utilized. Similarly, the residence time in the extruder is typically controlled to minimize decomposition. Residence times of up to about 2 minutes or more may be employed, with up to about 1.5 minutes used in one embodiment, and up to about 1 minute used in another exemplary embodiment. Prior to extrusion into the desired form (typically pellets, sheet, web, or the like, the resulting mixture can optionally be filtered, such as by melt filtering and/or the use of a screen pack, or the like, to remove undesirable contaminants or decomposition products.

The authenticatable polymers may be used for any application in which the physical and chemical properties of the material are desired. In one embodiment, the authenticatable polymers are used to make formed articles such as data storage media. In one exemplary embodiment, the authenticatable polymers will be used to make data storage media such as CDs and DVDs. Other embodiments include packaging material (and especially drug packaging), automotive parts like lenses, telecom accessories (like cell phone covers), computers and consumer electronics, construction materials, medical devices, eyewear products, secure documents including passports and ID cards, credit cards, films and sheets (including those used in display applications) and the like.

After the authenticatable polymer composition has been produced, it may be formed into a data storage media using various molding techniques, processing techniques, or combination thereof. Possible molding techniques include injection molding, film casting, extrusion, press molding, blow molding, stamping, and the like. One possible process comprises an injection molding-compression technique where a mold is filled with a molten polymer. The mold may contain a preform, inserts, fillers, etc. The authenticatable polymer is cooled and, while still in an at least partially molten state, compressed to imprint the desired surface features (e.g., pits, grooves, edge features, smoothness, and the like), arranged in spiral concentric or other orientation, onto the desired portion(s) of the formed part, i.e. one or both sides in the desired areas. The formed part is then cooled to room temperature. Once the formed part has been produced, additional processing, such as electroplating, coating techniques (spin coating, spray coating, vapor deposition, screen printing, painting, dipping, and the like), lamination, sputtering, and combinations comprising a of the foregoing processing techniques, among others known in the art, may be employed to dispose desired layers on the substrate.

An example of a polycarbonate data storage media comprises an injection molded polycarbonate substrate that may optionally comprise a hollow (bubbles, cavity, and the like) or filled (metal, plastics, glass, ceramic, and the like, in various forms such as fibers, spheres, particles, and the like) core.

In one embodiment when a formed authenticatable or test article is a data storage media, the authenticatable polymer will preferably be used to form the substrate(s) that will be read through by a laser in a data storage media player device. The reason is that it is significantly more difficult to fake the response of an authenticatable polymer and ensure that the technology used does not impact playability of the media. In a data storage media having two substrates, such as a DVD, one or both substrates can be formed using the authenticatable polymers. In one exemplary embodiment, the substrate of a DVD formed of the authenticatable polymer may be the layer read by a laser in a DVD player device. Additional format include DVD-R, DVD+R, DVD-RW, DVD+RW, DVD-Rom, DVD-Ram, Blu-Ray, HD-DVD (high density DVD) and EVD (enhanced video discs).

Disposed on the substrate are various layers including: a data layer, dielectric layer(s), a reflective layer(s), and/or a protective layer, as well as combinations comprising the foregoing layers. These layers comprise various materials and are disposed in accordance with the type of media produced.

For example, for a first surface media, the layers may be protective layer, dielectric layer, data storage layer, dielectric layer, and then the reflective layer disposed in contact with the substrate, with an optional decorative layer disposed on the opposite side of the substrate. Meanwhile, for an optical media, the layers may be optional decorative layer, protective layer, reflective layer, dielectric layer, and data storage layer, with a subsequent dielectric layer in contact with the substrate. Optical media may include, but is not limited to, any conventional pre-recorded, re-writable, or recordable formats such as: CD, CD-R, CD-RW, DVD, DVD-R, DVD-RW, DVD+RW, DVD-RAM, high-density DVD (HD-DVD), enhanced video disks (EVD), magneto-optical, and others. It is understood that the form of the media is not limited to disk-shape, but may be any shape which can be accommodated in a readout device.

The data storage layer(s) may comprise any material capable of storing retrievable data, such as an optical layer, magnetic layer, or a magneto-optic layer. Typically the data layer has a thickness of up to about 600 Angstroms (Å) or so, with a thickness up to about 300 Å preferred. Possible data storage layers include, but are not limited to, oxides (such as silicone oxide), rare earth elements-transition metal alloys, nickel, cobalt, chromium, tantalum, platinum, terbium, gadolinium, iron, boron, others, and alloys and combinations comprising a of the foregoing, organic dye (e.g., cyanine or phthalocyanine type dyes), and inorganic phase change compounds (e.g., TeSeSn, InAgSb, and the like).

The protective layer(s), which protect against dust, oils, and other contaminants, can have a thickness of greater than about 100 microns ($\mu$) to less than about 10 Å in one embodiment, with a thickness of about 300 Å or less in other embodiments, and a thickness of about 100 Å or less in other exemplary embodiments. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising a of the foregoing.

The dielectric layer(s), which are disposed on one or both sides of the data storage layer and are often employed as heat controllers, can typically have a thickness of up to or exceeding about 1,000 Å and as low as about 200 Å or less. Possible dielectric layers include nitrides (e.g., silicon nitride, aluminum nitride, and others); oxides (e.g., aluminum oxide); carbides (e.g., silicon carbide); and combinations comprising of the foregoing materials, among other materials compatible within the environment and preferably not reactive with the surrounding layers.

The reflective layer(s) should have a sufficient thickness to reflect a sufficient amount of energy (e.g., light) to enable data retrieval. Typically the reflective layer(s) can have a thickness of up to about 700 Å or so, with a thickness of about 300 Å to about 600 Å being used in some exemplary embodiments. Possible reflective layers include any material capable of reflecting the particular energy field, including metals (e.g., aluminum, silver, gold, titanium, silicon, and alloys and mixtures comprising a of the foregoing metals, and others).

In addition to the data storage layer(s), dielectric layer(s), protective layer(s) and reflective layer(s), other layers can be employed such as lubrication layer and others. Useful lubricants include fluoro compounds, especially fluoro oils and greases, and the like.

In one embodiment, the authenticatable polymers may be formed into the substrate of a data storage media. In one exemplary embodiment, the authenticatable polymer may comprise the substrate of an optical storage media. In one particularly exemplary embodiment, the authenticatable polymer may comprise at least one substrate of a digital versatile disk (DVD).

Illustrative DVDs comprising the authenticatable polymers disclosed herein comprise two bonded plastic substrates (or resin layers), each typically having a thickness less than or equal to about 1.0 millimeter (mm), with a thickness of less than or equal to about 0.7 mm preferred. A thickness of greater than or equal to about 0.4 mm is also preferred. At least one of the two bonded plastic substrates comprises one or more layers of data. The first layer, generally called layer zero (or L0), is closest to the side of the disk from which the data is read (readout surface). The second layer, generally called layer 1 (L1), is further from the readout surface. Disposed between L0 (3) and L1 (5) are typically an adhesive and optionally a protective coating or separating layer. Single sided DVD's (i.e., those that will be read from a single readout surface disposed on one side of the DVD), can additionally comprise a label disposed on the side of the DVD opposite the readout surface. In one embodiment, one or both of the first layer and the second layer will be comprised of the authenticatable polymers. In one exemplary embodiment, the first layer will be comprised of the authenticatable polymer.

In the case of a single layer read from a readout surface (e.g. DVD 5, DVD 10), a stamped surface is covered with a thin reflective data layer by a sputtering or other deposition process. This creates a metallic coating typically about 60 to about 100 angstroms (Å) thick. For two data layer DVDs that are read from the same readout surface (e.g. DVD 9, DVD 14, DVD 18), the laser must be able to reflect from the first layer when reading it, but also focus (or transmit) through the first layer when reading the second layer. Therefore, the first layer is "semi-transparent" (i.e., semi-reflective), while the second layer is "fully-reflective". Under current standards set by the Consortium for Optical Media, metallization combination for the fully-reflective and semi-reflective data layers, as measured per the electrical parameter R14H (as described in ECMA specifications #267), should be about 18 percent (%) to about 30% at the wavelength of the laser. In the present DVD'S, the laser wavelength generally employed is less than or equal to about 700 nm, with about 400 nm to about 675 nm preferred, and about 600 nm to about 675 nm more preferred. Although these metallization standards were set for DVD data layers employed with colorless, optical quality resin, they are equally applied to DVD systems with colored resin.

When color is added to the resin, light transmission through and reflected from the substrate is effected. The metallization nature and thickness on the semi-reflective and fully reflective (L0 and L1) layers is adapted for the light transmission of the substrate. Desired reflectivity can be obtained by balancing the metallization thickness with the reflectivity of the semi-reflective data layer, and by adjusting the thickness of the fully reflective data layer to ensure its reflectivity is within the desired specification.

Metallization for the individual data layer(s) can be obtained using various reflective materials. Materials, e.g., metals, alloys, and the like, having sufficient reflectivity to be employed as the semi-reflective and/or fully reflective data layers, and which can preferably be sputtered onto the substrate, can be employed. Some possible reflective materials comprise gold, silver, platinum, silicon, aluminum, and the like, as well as alloys and combinations comprising at least one of the foregoing materials. For example, the first/second reflective data layer metallization can be gold/aluminum, silver alloy/aluminum, silver alloy/silver alloy, or the like.

In addition to the overall reflectivity of each layer, the difference in reflectivity between subsequent reflective data layers should be controlled, in order to ensure sufficient reflectivity of the subsequent layer. Preferably, the difference in reflectivity between subsequent layers (e.g., the first and second layers) is less than or equal to about 5%, with less than or equal to about 4% preferred, and less than or equal to about 3.0% more preferred. It is further preferred to have a reflectivity difference between the adjacent reflective data layers of greater than or equal to about 0.5%, with greater than or equal to about 1% more preferred. It should be noted that although described in relation to two layers, it is understood that more than two layers could be employed, and that the difference in reflectivity between subsequent layers should be as set forth above.

The reflective data layers are typically sputtered or otherwise disposed on a pattern (e.g., surface features such as pits, grooves, asperities, start/stop orientator, and/or the like) formed into a surface of the substrate via molding, embossing, or the like. Depositions, for example, can comprise sputtering a semi-reflective data layer over a first patterned surface. A separator layer or protective coating can then be disposed over the semi-reflective data layer. If a multiple data layer DVD (e.g., DVD 14, DVD 18, or the like) is to be formed, a $2^{nd}$ patterned surface can be formed (e.g., stamped or the like) in the side of the separator layer opposite the semi-reflective data layer. A fully reflective data layer can then be sputtered or otherwise deposited on the separator layer. Alternatively, for DVD 14 construction, the fully reflective data layer can be deposited on a patterned surface of a $2^{nd}$ substrate (or resin layer). A separate layer or protective coating is then disposed on one or both of the semi-reflective data layer and the fully reflective data layer. A bonding agent or adhesive can then be disposed between the two substrates and they can be bonded together to form a disk. Optionally, several semi-reflective data layers can be deposited with a separator layer between each subsequent layer.

The reflectivity of the reflective data layer(s) can be about 5% to about 100%, depending upon the number of reflective layers. If a single reflective data layer is employed, the reflectivity is preferably about 30% to about 100%, with about 35% to about 90% more preferred, and about 45% to about 85% even more preferred. If a dual reflective data layer is employed, the reflectivity of the data layers is preferably about 5% to about 45%, with about 10% to about 40% more preferred, about 15% to about 35% even more preferred, and about 18% to about 30% especially preferred. Finally, if multiple reflective data layers (e.g., greater than 2 reflective data layers readable from a single reading surface) are employed, the reflectivity is preferably about 5% to about 30%, with about 5% to about 25% more preferred. The especially preferred ranges are currently based upon the ECMA specification #267, wherein the reflectivity is either about 18% to about 30% reflectivity for a dual layered DVD (e.g., at least one fully reflective layer and at least one semi-reflective layer) or about 45% to about 85% reflectivity for a single layer DVD (e.g., one fully reflective layer).

In one embodiment, the authenticatable polymers used to make these DVD substrates will enables the transmission of about 60% to less than 94% of light through, in the wavelength region of the laser. Within that transmission range, preferably, the transmissivity is greater than or equal to about 70%, with greater than or equal to about 74% more preferred, and greater than or equal to about 78% especially preferred. Depending upon the type and amount of colorant employed, the transmissivity can be less than or equal to about 92%, with less than or equal to about 88% and even less than or equal to about 85% possible, depending upon the type of colorant. It should be noted that as the transmissivity of the substrate decreases, the ability to attain the desired adhesion of the substrates becomes more difficult. Preferably, the substrate comprises polycarbonate, with a primarily polycarbonate (e.g., greater than or equal to about 80% polycarbonate) substrate especially preferred.

The disclosure also provides a method of making an article. The method comprises providing an authenticable polymer comprising the authenticable compound of formula I and forming an authenticable article from the authenticatable polymer. Various molding techniques may be employed to fabricate the article. Suitable molding techniques include injection molding, film casting, extrusion, press molding, blow molding, stamping, and the like.

EXPERIMENTAL

The nuclear magnetic resonance (NMR) spectra of the authenticatable compounds of formula I were recorded using Bruker 300 MHz Avance spectrometer using CDCl$_3$ or DMSO-d$_6$ as a solvent.

High performance liquid chromatography (HPLC): The samples were analyzed using 5 methods. Micromass Quattro Ultima Pt (4000 amu) Mass spectrometer attached to Waters Alliance HPLC instrument system was used for methods I to IV. Shimadzu HPLC Class-VP instrument system was used for method V. For the ionization either Electrospray ionization (ESI) or Atmospheric chemical ionization (APCI) technique were used depending on the nature of the compound. Separation of the compound was done by reverse phase chromatography followed by MS analysis. Methods I, II and III employed a RP Xterra column-C18 (a HPLC column manufactured by Waters, USA), 4.6×50 millimeters (mm), 5 micrometers (μm), and the solvent gradient set forth in Table 1, Table 2 and Table 3 respectively. Method IV employed a RP Xterra column-C18 (a HPLC column manufactured by Waters, USA), 4.6×50 millimeters (mm), 5 micrometers and solvent as Acetonitrile with run time of 15 minutes. Method V was run in (mm Zorbax Hypersil, 4.6×100 mm, 5 micrometers and the solvent gradient set forth in Table below. All these methods employed a flow rate of 1 milliliter per minute (ml/min), a column temperature of 30° C. and UV detector—PDA scan from 200 to 800 nm.

| Solvent Gradient | Time in minutes | % of water | % of Acetonitrile |
|---|---|---|---|
| | 0 | 80 | 20 |
| | 3 | 80 | 20 |
| | 15 | 10 | 90 |
| | 22 | 10 | 90 |
| | 23 | 80 | 20 |
| | 30 | 80 | 20 |

Thermogravimetric analysis: The compounds prepared in the Examples 1-16 described below were subjected to thermogravimetric analysis (also referred to as "TGA"), which measures the amount of weight change in a material as a function of temperature in a controlled atmosphere. TGA analyses were carried out using a TGA 2950 instrument equipped with an auto sampler, and available from TA Instruments. The sample was equilibrated to an initial temperature of 40° C., then heated at the rate of 10° C. per minute upto a maximum temperature of 500° C., and thereafter equilibrated at 500° C. The weight of the sample was monitored continuously throughout this process. The technique measures any weight change that can occur during the heating process. Any weight loss is generally indicative of decomposition or degradation of the sample. This technique was used to measure the thermal stability of the compoundds disclosed herein. The TGA experiment gives a weight loss—temperature curve. Temperature at which 10% weight loss of compound is observed is considers as TGA.

Ultraviolet-Visible Spectroscopy measurements: The compounds of formula I and compounds of formula II were prepared and their Ultraviolet-Visible spectral characteristics were measured using methylene chloride (DCM) or Dimethyl formamide (DMF) solvents in the wavelength region of 300 nm to 800 nm using a double beam UV/VIS Perkin-Elmer Lambda 900 UV/VIS/NIR spectrophotometer. The absorption and emission maxima are included in the examples below.

Fluorescence measurements: Fluorescence properties of hydroxy chromones and protected chromones (fluorophores) were evaluated using Hitachi—F-4500 spectrophotometer. Molded Chips of 1 mm thickness having 0.005% of authenticatable compound along with poycarbonate formulation obtained by the above mentioned extrusion & molding experiments. Molded sample chips were placed in sample holder of spectrophotometer with reflective background and fluorescence response was measured by excitation at 365 nm wavelength.

The reaction contents and reagent used are laboratory grade chemicals obtained from Aldrich-Sigma Company, USA & Lancaster chemical co. UK.

EXAMPLES

Example 1

This Example describes the preparation of 3-hydroxy-2-phenyl-4H-chromen-4-one (sometimes referred to as 3-HF), a compound of formula II.

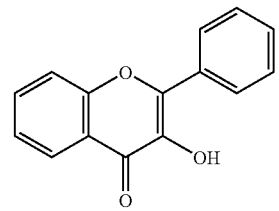

3-hydroxy-2-phenyl-4H-chromen-4-one

To a three necked round bottomed flask, equipped with reflux condenser, calcium chloride guard tube and nitrogen inlet and magnetic stirrer, was charged methanol (200 mililiters (ml)), benzaldehyde (10.6 grams (g)) and 2-hydroxy acetophenone (13.6 g). The mixture was cooled to 10-15° C. and sodium hydroxide (15 g in 40 milliliters (ml) water) was slowly added. The reaction mixture was stirred at room temperature (~25° C.) for 24 hours. Then methanol was added to the reaction mixture and the mixture was cooled to below 15° C. To this cooled mixuture sodium hydroxide (15 g in 40 ml water) and hydrogen peroxide (56 ml) were added and the reaction mixture was stirred for 6 to 8 hrs at room temperature. After this the reaction mixture was cooled to 10° C., neutralized using hydrochloric acid and the solid product that precipitated out was filtered. The solid was washed with water till the filtrate was free of acid. The solid product was dried in an oven at 70° C.

Yield: 11.8 g HPLC Purity (% A): 99.8% Mass: m/z 238

Determination of absorption and emission maxima under UV:

λabs 343 nm

λems. 528 μm

TGA: 54% weight loss at 300° C.

Example 2

This Example describes the preparation of 3-hydroxy-2-biphenyl-4H-chromen-4-one (sometimes referred to as BP-3-HF, a compound of formula II.

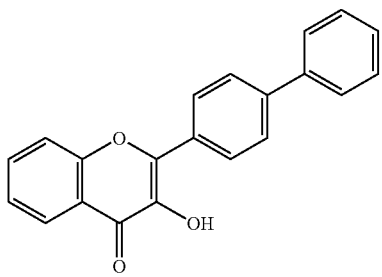

3-hydroxy-2-biphenyl-4H-chromen-4-one

To a three necked round bottomed flask, equipped with reflux condenser, calcium chloride guard tube and nitrogen inlet and magnetic stirrer, was charged methanol (200 ml), biphenyl-4-carboxaldehyde (2.73 g) and 2-hydroxy acetophenone (2.04 g). The reaction mixture was cooled to 10-15° C. and potassium hydroxide (6 g) was added slowly and the reaction was stirred at room temperature (~25° C.) for 24 hrs. Then methanol was added to the reaction and the reaction mixture was cooled below 15° C. and potassium hydroxide (6 g) and hydrogen peroxide (6.8 ml) were added to the reaction mixture and the reaction mixture was stirred for 6-8 hrs at room temperature. After this the reaction mixture was cooled to 10° C., neutralized using hydrochloric acid and the solid product that precipitated was filtered. The solid was washed with water till the filtrate is free of acid. The solid product was dried in oven at 70° C.

Example 3

This Example describes the preparation of 3-hydroxy-2-(4-(3-hydroxy-4-oxo-4H-chromen-2-yl)phenyl)-4H-chromen-4-one (sometimes referred to as bis-3-HF), a compound of formula II.

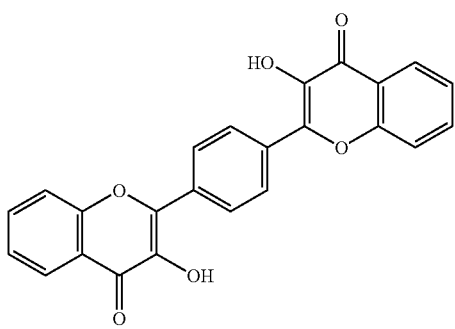

3-hydroxy-2-(4-(3-hydroxy-4-oxo-4H-chromen-2-yl)phenyl)-4H-chromen-4-one

To a three necked round bottomed flask, equipped with reflux condenser, calcium chloride guard tube and nitrogen inlet and magnetic stirrer, was charged methanol (200 ml), Terephthalaldehyde (0.98 g) and 2-hydroxy acetophenone (2.04 g). The reaction mixture was cooled to 10-15° C. and sodium hydroxide (3 g) was added slowly and the reaction was stirred at room temperature (~25° C.) for 24 hrs. Then methanol (200 ml) was added to the reaction and the reaction mixture was cooled below 15° C. and sodium hydroxide (3 g) and hydrogen peroxide (9 ml) were added to the reaction mixture and the reaction mixture was stirred for 6-8 hrs at room temperature. After this the reaction mixture was cooled to 10° C., neutralized using hydrochloric acid and the solid product that precipitated was filtered. The solid was washed with water till the filtrate is free of acid. The solid product was dried in oven at 70° C.

Yield: 1.1 g

HPLC Purity (% A): the product was subjected to HPLC analysis but it gets retained on the column therefore the chromatography of this molecule could not be done.

Determination of absorption and emission maxima

λabs. 364 nm

λems: 555.8 nm (Illustrated in FIG. 1):

TGA: Stable upto 300° C.

Example 4

This Example describes the preparation of 2-(benzofuran-2-yl)-3-hydroxy-4H-chromen-4-one (sometimes referred to as BF-3 HF, a compound of formula II.

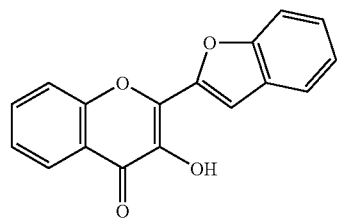

2-(benzofuran-2-yl)-3-hydroxy-4H-chromen-4-one

To a three necked round bottomed flask, equipped with reflux condenser, calcium chloride guard tube and nitrogen inlet and magnetic stirrer, was charged methanol (200 ml), 2-benzofuranaldehyde (1.46 g) and 2-hydroxy acetophenone (1.36 g). The reaction mixture was cooled to 10-15° C. and sodium hydroxide (4 g) was added slowly and the reaction was stirred at room temperature (~25° C.) for 24 hrs. Then methanol (200 ml) was added to the reaction and the reaction mixture was cooled below 15° C. and sodium hydroxide (4 g) and hydrogen peroxide (10 ml) were added to the reaction mixture and the reaction mixture was stirred for 6-8 hrs at room temperature. After this the reaction mixture was cooled to 10° C., neutralized using hydrochloric acid and the solid product that precipitated was filtered. The solid was washed with water till the filtrate is free of acid. The solid product was dried in oven at 70° C.

Yield: 1.1 g HPLC Purity (% A): 99% Mass: m/z 277.88

Determination of absorption and emission maxima:

λabs. 363 nm

λems. 500 nm

TGA: 32% loss at 300° C.

TABLE 1

| Example | Hydroxy Flavone | % Yield | % Purity (HPLC) | Absorption Max. (nm) | Visible Cut-off wavelength | Fluorescence Max. (nm) | Decomposition temp. ° C. |
|---|---|---|---|---|---|---|---|
| 1 | 3-HF | 49.57 | 99.8 | 343 | 380 | 528 | 220 |
| 2 | BP-3HF | 50.95 | 98.85 | 355 | 385 | 542 | 290 |
| 3 | Bis-3HF | 36.85 | NA* | 364 | 418 | 555.8 | >300 |
| 4 | BF-HF | 39.56 | 99 | 363 | 410 | 547 | 276 |

*Retained on HPLC column.

Example 5

This Example describes the preparation of 3-ethylcarbonate-2-(4-(3-ethylcarbonate-4-oxo-4H-chromen-2-yl)phenyl)-4H-chromen-4-one (sometimes referred to as ethyl bis HF), a compound of formula I.

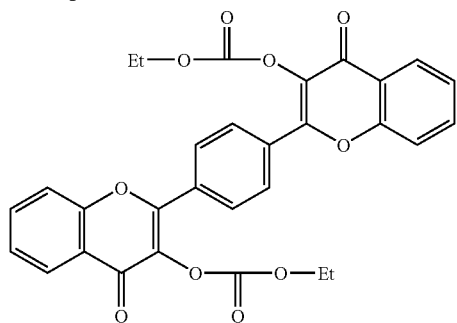

3-ethylcarbonate-2-(4-(3-ethylcarbonate-4-oxo-4H-chromen-2-yl)phenyl)-4H-chromen-4-one A mixture of 3-hydroxy-2-(4-(3-hydroxy-4-oxo-4H-chromen-2yl)phenyl)-4H-chromen-4-one (0.4 g), Triethylamine (0.17 g), Dichloromethane (20 ml) and Ethylchloroformate (0.54 g) was stirred at room temperature for about 10 hours. The solvent dichloromethane was then evaporated under vacuum at room temperature and then dried under high vacuum for 4 hours to give the desired product.

Yield: 0.45 g HPLC Purity (% A):99.5% Mass: m/z 542

Figure 2:
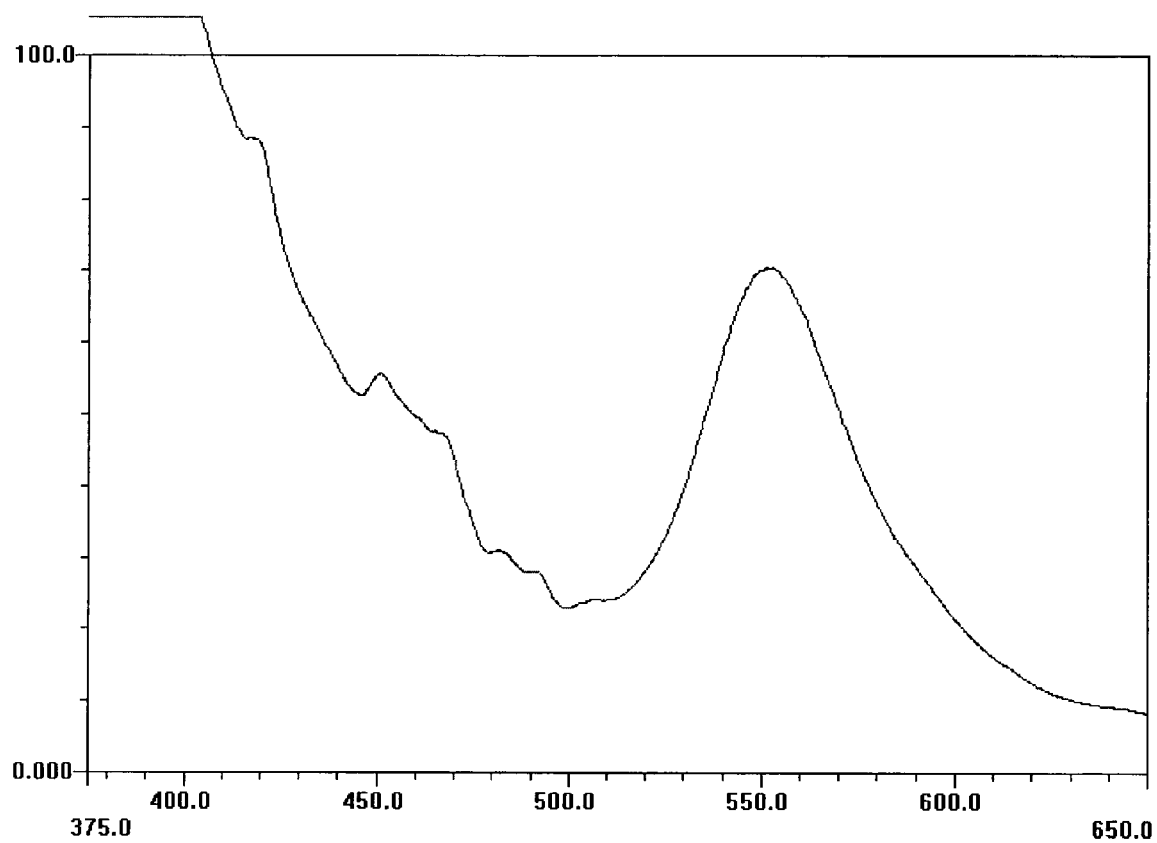
FIG. 2 represents the emission spectra for Ethyl-Bis-3HF. The fluorescence maximum is at a wavelength of about 553 and the corresponding intensity is about 71.

Determination of absorption and emission maxima:
λabs. 315 nm
λems. 553 nm (Illustrated in FIG. 2)

Example 6

This Example describes the preparation of 3-phenylcarbonate-2-(4-(3-phenylcarbonate-4-oxo-4H-chromen-2-yl)phenyl)-4H-chromen-4-one (sometimes referred to as phenyl bis-3HF), a compound of formula I.

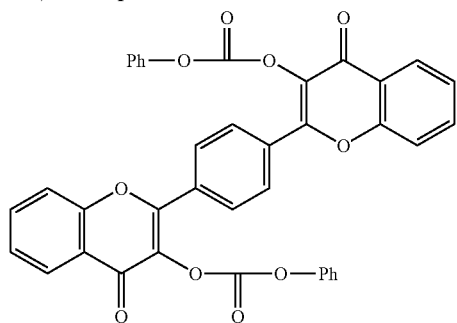

3-phenylcarbonate-2-(4-(3-phenylcarbonate-4-oxo-4H-chromen-2-yl)phenyl)-4H-chromen-4-one A mixture of 3-hydroxy-2-(4-(3-hydroxy-4-oxo-4H-chromen-2yl)phenyl)-4H-chromen-4-one (0.4 g), triethylamine (0.30 g), dichloromethane (20 ml) and phenyl chloroformate (0.31 g) was stirred at room temperature for about 10 hours. The reaction mixture was then filtered and gave 10 ml Dichloromethane wash to the filtered bed and then dried under high vacuum for 4 hours to give the desired product.

Yield: 67%.

Example 7

This example describes the preparation of 3 tertbutylcarbonate-2-(4-(3-tertbutylcarbonate-4-oxo-4H-chromen-2-yl)phenyl)-4H-chromen-4-one sometimes referred to as Boc bis-3 HF), a compound of formula I.

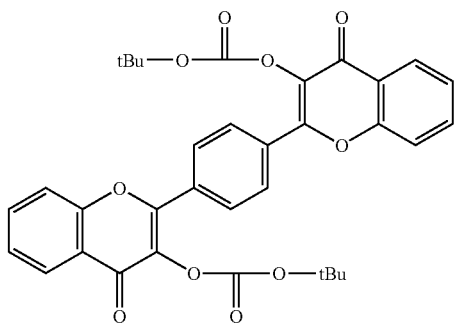

3-tertbutylcarbonate-2-(4-(3-tertbutylcarbonate-4-oxo-4H-chromen-2-yl)phenyl)-4H-chromen-4-one A mixture of 3-hydroxy-2-(4-(3-hydroxy-4-oxo-4H-chromen-2yl)phenyl)-4H-chromen-4-one (0.88 g), N,N'-Dimethylamino pyridine (0.12 g), Dichloromethane (40 milliliters (ml)) and di-tertiary-butyl dicarbonate (1.946 g) was stirred at room temperature for about 12 hours. Reaction mixture was then subjected to vacuum distillation to remove dichloromethane(~20 ml). Hexane (40 ml) was added to the residue to precipitate out the product. The reaction mixture was then filtered and was given 15 ml hexane wash to remove unreacted reactants and impurities to yield a pale yellow product.

Yield: 1.0 g HPLC Purity: 98% Mass: m/z 598

Example 8

This example describes the preparation of 3-tertbutylcarbonate-2-phenyl-4H-chromen-4-one (sometimes referred to as Boc-3HF), a compound of formula I.

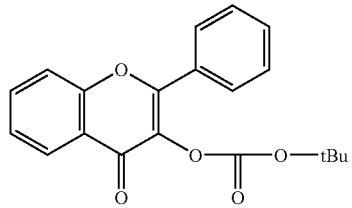

3-tertbutylcarbonate-2-phenyl-4H-chromen-4-one

A mixture of 3-hydroxy-2-phenyl-4H-chromen-4-one (0.92 gram), N,N'-dimethylamino pyridine (0.07 g), dichloromethane (30 ml.) and di-tertiary-butyl dicarbonate (1.690 g) was stirred at room temperature for about 4 hours. Reaction mixture was then subjected to vacuum distillation to remove dichloromethane (~15 ml) and hexane (30 ml) was added to precipitate out the product. The reaction mixture was then filtered and was given 15 ml hexane wash to remove unreacted reactant and impurities to obtain a pale yellow product.

Figure 3:
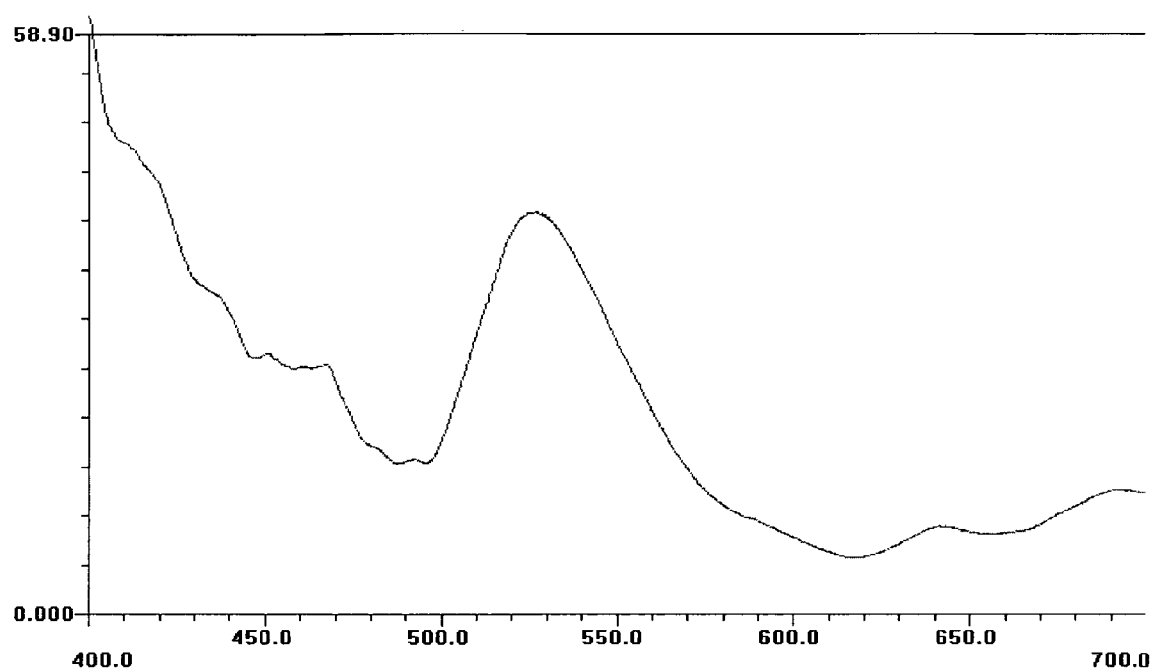
FIG. 3 represents the emission spectra for Boc-3HF. The fluorescence maximum is at a wavelength of about 527 nm when the excitation stimulus was at about 365 nm.

Yield: 0.98 g Purity by HPLC: 99% Mass spectra:-Mz-338. abs. 290 nm
λems. 527 nm (Illustrated in FIG. 3)

Example 9

This example describes the preparation of 3-terbutylcarbonate-2-biphenyl-4H-chromen-4-one (sometimes referred to as Boc-BP-3 HF), a compound of formula I.

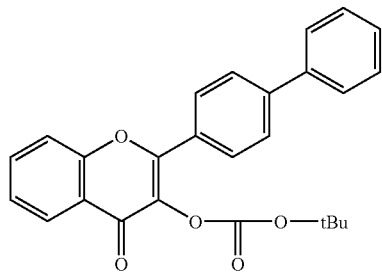

3-tertbutylcarbonate-2-biphenyl-4H-chromen-4-one

A mixture of 3-hydroxy-2-biphenyl-4H-chromen-4-one (0.98 gram), N,N'-dimethylamino pyridine (0.07 g), dichloromethane (30 ml) and di-tertiary-butyl dicarbonate (1.353 gin) was stuffed at room temperature for about 4-5 hours. Reaction mixture was then subjected to vacuum distillation to remove dichloromethane (~15 ml) and hexane (30 ml) was added to precipitate out the product. The reaction mixture was then filtered and was given 20 ml hexane wash to remove un reacted reactant and impurities to obtain a pale yellow product.

Yield: 1.02 g Purity by HPLC: 98% Mass spectra:-Mz-414.

Example 10

This example describes the preparation of carbonic acid tertiary-butyl ester 2-(benzofuran-2-yl)-3-tertbutylcarbonate-4H-chromen-4-one (sometimes referred to as Boc-BF-3 HF), a compound of formula I.

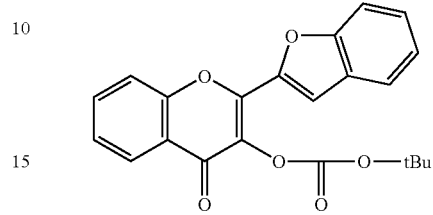

2-(benzofuran-2-yl)-3-tertbutylcarbonate-4H-chromen-4-one

A mixture of 2-(benzofuran-2-yl)-3-hydroxy-4H-chromen-4-one (BF-3 HF) (0.50 g), N,N'-dimethylamino pyridine (0.1 g), tri ethyl amine (0.30 ml), dichloromethane (30 ml) and di-tertiary-butyl dicarbonate (0.5 g) was stirred at room temperature for about 8-9 hours. Reaction mixture was then subjected to vacuum distillation to remove dichloromethane (~15 ml) and hexane (20 ml) was added to precipitate out the product. The reaction mixture was then filtered and was given 15 ml hexane wash to remove unreacted reactant and impurities to obtain an off white product.

Yield: 0.408 g Purity by HPLC: 99% Mass spectra:-Mz-378.

Example 11

This Example describes the preparation of bis(4-oxo-2-phenyl-4H-chromen-3-yl) terephthalate (sometimes referred to a ter-phthaloyl bis-3 HF), a compound of formula I.

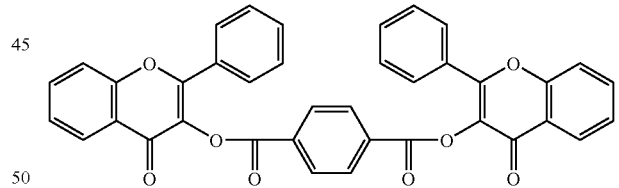

bis(4-oxo-2-phenyl-4H-chromen-3-yl) terephthalate

To the three-necked round bottom flask attached with reflux condenser, calcium chloride guard tube and nitrogen inlet, 3-hydroxy-2-phenyl-4H-chromen-4-one (0.59 g), terephthaloyl chloride (0.59 g) and dichloromethane (50 ml) were charged. Then triethyl amine (0.29 g) was charged and the reaction mixture was stirred at room temperature and monitored by thin layer chromatography (TLC). On completion of the reaction 10 ml water was added to the reaction mixture and the organic layer was separated. The organic layer was dried and evaporated under reduced pressure to give the product.

Yield: 0.645 g Purity: 76.92%

Table 2: This table summarizes the results of examples 5-11

TABLE 2

| Example | Protected Hydroxy Flavone | Yield in % | Purity (HPLC) % | Absorption Max. (nm) | Visible Cut-off wavelength | De-blocking Temp. ° C. |
|---|---|---|---|---|---|---|
| 5 | Ethyl-Bis-3HF | 83 | 99.5 | 315 | 368 | 190 |
| 6 | Phenyl-Bis-3HF | 67 | NA* | NA | NA | 195 |
| 7 | Boc-Bis-3HF | 74 | 98 | 318 | 398 | 180 |
| 8 | BOC-3HF | 76 | 99 | 290 | 341 | 185 |
| 9 | Boc-BP3HF | 75 | 98 | 314 | 366 | 185 |
| 10 | Boc-BF-3HF | 70 | 99 | 357 | 402 | 180 |
| 11 | Ter-Phthaloyl-Bis3HF | 43 | 76.9 | 290 | 340 | 365 |

*Retained on HPLC column, a -Not soluble in Solvent, could not get visible spectra Example 12-16

These examples provide additional protected hydroxy flavones prepared in a similar manner as discussed in examples 5-11. The results of the examples are tabulated in Table 3 below.

TABLE 3

| Example | Protected Hydroxy Flavone | Yield in % | Purity (HPLC) % | Absorption Max. (nm) | Visible Cut-off wavelength | De-blocking Temp. ° C. |
|---|---|---|---|---|---|---|
| 12 | Nitro-3HF | 59 | 96 | 288 | 340 | 190 |
| 13 | Phenyl-BP-3HF | 56 | 99.50 | 314 | 362 | 180 |
| 14 | Nitro-BP-3HF | 56 | 88.50 | 312 | 366 | 180 |
| 15 | Phenyl-BF-3HF | 72.50 | 99.00 | 340 | 393 | 130 |
| 16 | Nitro-BF-3HF | 43 | 79 | 357 | 402 | 185 |

Example 17

This example describes the general procedure used for preparing extruded polymer samples incorporating the heat and/or photo and/or chemically labile security materials described above.

A 1 kilogram sample of bisphenol A homopolycarbonate and the authenticable compound 0.0005 weight percent 3-tertbutylcarbonate-2-biphenyl-4H-chromen-4-one (sometimes referred to as Boc-BP-3 HF) of the overall sample, was taken in a polyethylene bag and shaken vigorously for about 3-4 minutes. The resulting material was then compounded using a W & P ZSK-25 Mega compounder under vacuum at the conditions specified in Table 1 to produce colored polymer pellets.

TABLE 4

| | |
|---|---|
| Feed zone temperature (° C.) | 128 |
| Zone 1 temperature (° C.) | 280 |
| Zone 2 temperature (° C.) | 285 |
| Zone 3 temperature (° C.) | 285 |
| Zone 4 temperature (° C.) | 290 |
| Throat/Die temperature (° C.) | 290 |
| Screw speed (Revolutions per minute) | 300 |
| Temperature of Melt (° C.) | 300 |
| Torque (Nm) | 58-62 |

Example 18

This Example describes the general procedure used for producing molded chips from the extruded pellets prepared as described in Example 17.

The extruded pellets prepared as described in Example 17 were dried in an oven maintained at 120° C. for about 4 hours. Then the dried pellets were subjected to molding using a LTM-Demag molding machine under the conditions enumerated in Table 5.

TABLE 5

| | |
|---|---|
| Feed zone temperature (° C.) | 110 |
| Zone 1 temperature (° C.) | 300 |
| Zone 2 temperature (° C.) | 290 |
| Zone 3 temperature (° C.) | 275 |
| Nozzle Temperature (° C.) | 295 |
| Temperature of Melt (° C.) | 300 |
| Mold temperature (° C.) | 85 |
| Sample drying time (hours) | 4 |
| Sample drying temperature (° C.) | 120 |
| Cycle time (seconds) | 125 |
| Injection time (seconds) | 1.2 |
| Injection speed (revolutions per minute) | 25 |
| Injection pressure (bar) | 50 |
| Screw speed (Revolutions per minute) | 300 |
| Holding pressure (bar) | 40 |
| Holding time (seconds) | 10 |
| Cooling time (seconds) | 15 |
| Thickness of step chip inserts (millimeters) | 1, 2, and 3 |
| Thickness of single insert (millimeters) | 2.54 |

Example 19

This example describes a general procedure wherein a chemical stimulus was used as a deblocking stimulus i.e. acid as a de-blocking agent for compound of formula I. The acid was added at the polymer processing stage while incorporating a compound of formula I into a polymer matrix. Molded chips were then produced from the extruded pellets as described in Example 17.

A 1 kilogram sample of bisphenol A homopolycarbonate and the authenticable compound 0.005 weight percent 3-tertbutylcarbonate-2-biphenyl-4H-chromen-4-one of the overall sample and 10 ppm of phosphoric acid, was taken in a polyethylene bag and shaken vigorously for about 3-4 minutes. The resulting material was then compounded using a W & P ZSK-25 Mega compounder under vacuum at the conditions specified in Table 4 to produce colored polymer pellets.

Figure 4:
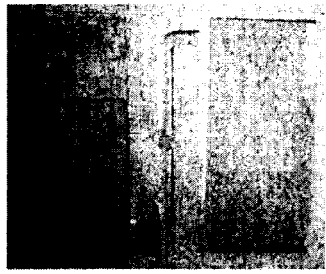
FIG. 4 is a color photograph illustrating the effect of incorporation of compound I (A) and compound II (B) independently in a polycarbonate
a. in the presence of day light and
b. after excitation under ultraviolet light at about 365 nm.
Figure 4:
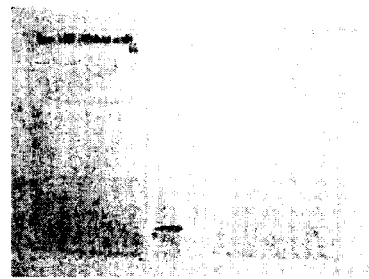
Figure 4:
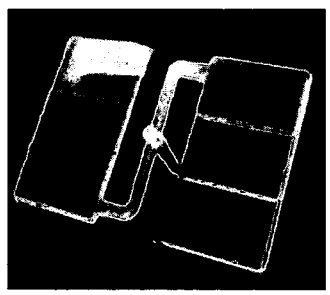
Figure 4:
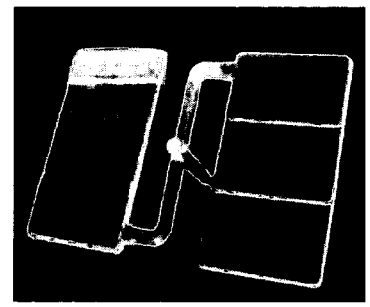

The molded articles were then placed under UV-visible light at 365 nm. The emission obtained is indicated in Table 6 below. Table 6 shows the intensity of the response at the maximum wavelength $\lambda_{max}$ for compounds of formula I prepared as per examples 5-16 that have been subjected to the deblocking stimulus and the excitation stimulus. Representative example illustrated in FIG. 4.

TABLE 6

| Example | Protected Hydroxy Flavone | Fluorescence Max. (nm) | Fluorescence Intensity in % | Deblocked status |
|---|---|---|---|---|
| 5 | Ethyl-Bis-3HF | 553.8 | 23 | Partially deblocked |
| 6 | Phenyl-Bis-3HF | 553.8 | 67.50 | Partially deblocked |
| 7 | Boc-Bis-3HF | 553.8 | 100 | Completely deblocked |
| 8 | BOC-3HF | 542 | 100 | Completely deblocked |
| 9 | Boc-BP3HF | 542 | 100 | Completely deblocked |
| 10 | Boc-BF-3HF | 547 | 100 | Completely deblocked |
| 11 | Ter-Phthaloyl-Bis-3HF | 528 | 00 | No deblocking under Processing condition |
| 12 | Nitro-3HF | 542 | 100 | Completely deblocked |
| 13 | Phenyl-BP-3HF | 542 | 100 | Completely deblocked |
| 14 | Nitro-BP-3HF | 542 | 51.98 | Partially deblocked |
| 15 | Phenyl-BF-3HF | 547 | 83.7 | Partially deblocked |
| 16 | Nitro-BF-3HF | 547 | 100 | Completely deblocked |

The data indicates that when the intensities of the emission spectrum match the intensities of the unblocked molecule when the protecting group is totally deblocked. However the intensities are lower when the protecting group is partially deblocked.

Example 20

Nitro-BF-3HF and 3HF phenylcarbonate were respectively mixed with a BPA polycarbonate optical quality resin (Lexan OQ1030) at a loading of about 0.1 wt %. After compounding using a twin-screw extruder in conditions similar to those presented in Table 5, articles were produced in the form of color chips. After molding the color chips exhibited no visible color under daylight but the Nitro-BF-3HF formulation yielded a yellow fluorescence while the 3HF phenylcarbonate formulation produced a green emission indicating at least partial deblocking during extrusion and/or molding. The chips were then exposed to a solid state Nd:YAG laser (10 mW power, 355 nm wave, made by Nanolase, France). The laser beam was collimated using fiber optic probes (Ocean Optics, USA) on each chip to form a spot for about 2 seconds for the Nitro-BF-3HF sample and about 10 seconds for the 3HF phenyl carbonate. The beam was moved using an automated x-y stage to form a pattern in the form of a General Electric logo with a diameter of about 0.5 mm. After exposure to the 355 nm wavelength, the chips remained colorless in both cases under daylight exposure. However, under a long range UV lamp with a maximum emission around 365 nm (excitation stimulus), the logo was revealed as a dark mark with a yellow and a green fluorescent background respectively. This example illustrates the ability to use the compounds of this invention to create cover patterns that could be used to authenticate products. Illustrated in FIG. 5.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A composition comprising a compound selected from the group consisting of 3-ethylcarbonate-2-(4-(3-ethylcarbonate-4-oxo-4H-chromen-2-yl)phenyl)-4H-chromen-4-one, 3-phenylcarbonate-2-(4-(3-phenylcarbonate-4-oxo-4H-chromen-2-yl)phenyl)-4H-chromen-4-one, 3 tertbutylcarbonate-2-(4-(3-tertbutylcarbonate-4-oxo-4H-chromen-2-yl)phenyl)-4H-chromen-4-one; 3-tertbutylcarbonate-2-phenyl-4H-chromen-4-one; 3-tertbutylcarbonate-2-biphenyl-4H-chromen-4-one; 2-(benzofuran-2-yl)-3-tertbutylcarbonate-4H-chromen-4-one, and bis(4-oxo-2-phenyl-4H-chromen-3-yl) terephthalate.

2. The composition of claim 1, wherein the compound is 3-ethylcarbonate-2-(4-(3-ethylcarbonate-4-oxo-4H-chromen-2-yl)phenyl)-4H-chromen-4-one.

3. The composition of claim 1, wherein the compound is 3-phenylcarbonate-2-(4-(3-phenylcarbonate-4-oxo-4H-chromen-2-yl)phenyl)-4H-chromen-4-one.

4. The composition of claim 1, wherein the compound is 3 tertbutylcarbonate-2-(4-(3-tertbutylcarbonate-4-oxo-4H-chromen-2-yl)phenyl)-4H-chromen-4-one.

5. The composition of claim 1, wherein the compound is 3-tertbutylcarbonate-2-phenyl-4H-chromen-4-one.

6. The composition of claim 1, wherein the compound is 3-tertbutylcarbonate-2-biphenyl-4H-chromen-4-one.

7. The composition of claim 1, wherein the compound is 2-(benzofuran-2-yl)-3-tertbutylcarbonate-4H-chromen-4-one.

8. The composition of claim 1, wherein the compound is bis(4-oxo-2-phenyl-4H-chromen-3-yl) terephthalate.

9. The composition of claim 1, further comprising a polymer.

10. The composition of claim 9, wherein the polymer is a polycarbonate.

* * * * *

UNITED STATES PATENT AND TRADEMARK OFFICE
CERTIFICATE OF CORRECTION

PATENT NO.        : 7,635,778 B2                                        Page 1 of 1
APPLICATION NO.   : 11/015352
DATED             : December 22, 2009
INVENTOR(S)       : Chauhan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Ninth Day of November, 2010

David J. Kappos
*Director of the United States Patent and Trademark Office*